United States Patent
Ying et al.

(10) Patent No.: US 11,098,331 B2
(45) Date of Patent: Aug. 24, 2021

(54) METHOD FOR PRODUCING LYSINE BY UTILIZING ADSORPTION AND IMMOBILIZED FERMENTATION OF RECOMBINANT CORYNEBACTERIUM GLUTAMICUM

(71) Applicant: Nanjing Tech University, Jiangsu (CN)

(72) Inventors: Hanjie Ying, Jiangsu (CN); Dong Liu, Jiangsu (CN); Yong Chen, Jiangsu (CN); Pingkai Ouyang, Jiangsu (CN); Qingguo Liu, Jiangsu (CN); Huanqing Niu, Jiangsu (CN); Bin Yu, Jiangsu (CN); Xiwei Peng, Jiangsu (CN); Ming Lei, Jiangsu (CN); Xingyuan Cao, Jiangsu (CN)

(73) Assignee: Nanjing Tech University, Jiangsu (CN)

( * ) Notice: Subject to any disclaimer, the term of this patent is extended or adjusted under 35 U.S.C. 154(b) by 0 days.

(21) Appl. No.: 17/117,788

(22) Filed: Dec. 10, 2020

(65) Prior Publication Data

US 2021/0147887 A1 May 20, 2021

(30) Foreign Application Priority Data

Mar. 13, 2020 (CN) .......................... 202010176582.4

(51) Int. Cl.
| | |
|---|---|
| *C12P 13/08* | (2006.01) |
| *C12N 11/084* | (2020.01) |
| *C12N 11/096* | (2020.01) |
| *C12N 9/14* | (2006.01) |
| *C12N 9/22* | (2006.01) |
| *C12N 11/12* | (2006.01) |
| *C12N 11/14* | (2006.01) |

(52) U.S. Cl.
CPC ................ *C12P 13/08* (2013.01); *C12N 9/14* (2013.01); *C12N 9/22* (2013.01); *C12N 11/084* (2020.01); *C12N 11/096* (2020.01); *C12N 11/12* (2013.01); *C12N 11/14* (2013.01); *C12Y 306/01003* (2013.01)

(58) Field of Classification Search
CPC .... C12N 11/14; C12N 15/77; C12N 2310/20; C12N 9/14; C12N 9/22; C12N 11/084; C12N 11/096; C12N 11/12; C12Y 306/01003; C12P 13/08

See application file for complete search history.

(56) References Cited

U.S. PATENT DOCUMENTS

| | | | | |
|---|---|---|---|---|
| 2004/0063115 | A1* | 4/2004 | Tang ..................... | C07H 21/04 435/6.16 |
| 2007/0202506 | A1* | 8/2007 | Stropp ........... | C12Y 306/03009 435/6.16 |
| 2012/0258518 | A1* | 10/2012 | Garcia-Moreno ..... | C07K 14/31 435/199 |
| 2018/0355344 | A1* | 12/2018 | Wang ..................... | C12N 15/63 |
| 2019/0256553 | A1* | 8/2019 | Levin ..................... | C12N 13/00 |

OTHER PUBLICATIONS

Wendisch. J Microbiol. Biotechnol. 16(7), 999-1009 (Year: 2006).*

* cited by examiner

*Primary Examiner* — Blaine Lankford

(74) *Attorney, Agent, or Firm* — Rankin, Hill & Clark LLP

(57) ABSTRACT

The invention discloses a method for producing lysine by utilizing adsorption and immobilized fermentation of a recombinant *Corynebacterium glutamicum*, wherein the recombinant *Corynebacterium glutamicum* is constructed by simultaneously overexpressing an adenosine triphosphate ATPase while knocking out an extracellular nuclease ExeR in a *Corynebacterium glutamicum*. The recombinant *Corynebacterium glutamicum* can effectively improve eDNA secretion of the *Corynebacterium glutamicum* and reduce eDNA degradation of the *Corynebacterium glutamicum*, so that the *Corynebacterium glutamicum* can be more easily adsorbed on a surface of a solid carrier for immobilized fermentation, such that a yield of continuous immobilized fermentation of the *Corynebacterium glutamicum* is increased by 49.67% than that of free fermentation of an original bacterium, and a fermentation cycle is shortened by 29.17%.

8 Claims, 4 Drawing Sheets

Specification includes a Sequence Listing.

Original bacterium          Recombinant bacterium

METHOD FOR PRODUCING LYSINE BY UTILIZING ADSORPTION AND IMMOBILIZED FERMENTATION OF RECOMBINANT CORYNEBACTERIUM GLUTAMICUM

TECHNICAL FIELD

The present invention belongs to the field of microorganism and fermentation engineering technologies, and more particularly, relates to a method for producing lysine by utilizing adsorption and immobilized fermentation of a recombinant *Corynebacterium glutamicum*.

BACKGROUND

As an amino acid of an aspartic acid family, L-lysine is one of the essential amino acids for human beings and animals that cannot be synthesized by the human beings and the animals, and is widely used in feed additives, food fortifiers and pharmaceutical products, wherein more than 90% lysine products are used as the feed additives.

A biofilm widely exists in nature. In a process of biofilm formation, an extracellular polymeric substance (EPS) secreted by a bacterium itself is a material basis of the biofilm formation, which has a characteristic of layered distribution, and plays a key role in adhesion and aggregation of the bacterium.

A continuous immobilized fermentation technology has been put into production now, wherein the continuous immobilized fermentation performed by the biofilm has achieved initial success. However, there are few reports of continuous immobilized fermentation based on the biofilm in a *Corynebacterium glutamicum*.

As an important industrial strain, the *Corynebacterium glutamicum* has a very weak film-forming ability, and is difficult to realize continuous fermentation. Therefore, we need to perform molecular modification on the *Corynebacterium glutamicum* to enhance a film-forming effect thereof, so as to realize later continuous immobilized fermentation.

Studies have shown that eDNA can increase initial adhesion of a bacterium to a carrier and initial adhesion between the bacteria themselves, thus promoting later formation of the biofilm and stabilizing a structure of the biofilm. The formation of the biofilm starts from a first batch of cells to the carrier, and the cells begin to secrete DNA. As an adhesive between the carrier and the cells, the DNA enables the cells to be not separated from the carrier, and then a distance between the cells is narrowed in the same way. Then the cells will secrete polysaccharides and proteins to consolidate a reticular structure formed by the DNA, so that the biofilm is not easy to be destroyed.

There have been patents previously reporting a *Corynebacterium glutamicum* overexpressing an adenosine triphosphate ATPase and a *Corynebacterium glutamicum* knocking out an extracellular nuclease ExeR. Strains used in the two patents are both used to produce proline. A metabolic pathway, a producing strain and fermentation conditions of the proline are quite different from the lysine. In this study, researchers studied a fermentation process of the lysine producing strain. Through a large number of experiments, it was found that operating only one gene had limited improvement on a yield of the lysine, while operating two genes simultaneously significantly improved the yield of the lysine. Therefore, in order to further improve the yield of the lysine, the extracellular nuclease gene ExeR of the lysine producing strain was knocked out, and meanwhile, expression of the adenosine triphosphate ATPase was enhanced. The inventors also studied an immobilized batch fermentation method suitable for the recombinant bacterium, so that the yield of the lysine by the immobilized fermentation of the recombinant glutamicum was increased by 49.67% than that of free fermentation of an original bacterium, and a fermentation performance was obviously superior to the *Corynebacterium glutamicum* which only knocked out the extracellular nuclease ExeR and the *Corynebacterium glutamicum* which only overexpressed the adenosine triphosphate ATPase.

SUMMARY

Objective of the present invention: a technical problem to be solved by the present invention is to provide a recombinant *Corynebacterium glutamicum* for producing lysine aiming at the defects of the prior art, in order to improve an immobilized film-forming ability of a *Corynebacterium glutamicum* and solve problems that a lysine producing strain in the prior art has a weak film-forming ability and cannot be used for continuous immobilized fermentation.

A technical problem to be further solved by the present invention is to provide a method for producing lysine by utilizing continuous immobilized fermentation of the recombinant *Corynebacterium glutamicum* mentioned above, so as to solve a problem that a single-batch fermentation cycle of the *Corynebacterium glutamicum* is too long, shorten the single-batch fermentation cycle of the *Corynebacterium glutamicum*, and have more obvious advantages in the continuous immobilized fermentation.

Idea of the present invention: in order to increase an amount of eDNA so as to enhance an immobilized film-forming ability of a strain, an extracellular nuclease gene ExeR of a *Corynebacterium glutamicum* is knocked out first, and then a protein adenosine triphosphate ATPase of a type IV secretion system is overexpressed on the basis of knocking out the ExeR, thus promoting secretion of the DNA and enhancing a film-forming effect.

In order to solve the foregoing technical problems, the present invention discloses a recombinant *Corynebacterium glutamicum*, wherein an extracellular nuclease ExeR of the recombinant *Corynebacterium glutamicum* is inactivated, and meanwhile, an expression of an adenosine triphosphate ATPase is enhanced. The recombinant *Corynebacterium glutamicum* is constructed by simultaneously overexpressing an adenosine triphosphate ATPase while knocking out an extracellular nuclease ExeR in a *Corynebacterium glutamicum*.

The simultaneously overexpressing the adenosine triphosphate ATPase while knocking out the extracellular nuclease ExeR means inactivating the ExeR gene in a genome of the *Corynebacterium glutamicum* by a gene knockout or gene inactivation technology, and enhancing expression of a gene of the ATPase enzyme in the *Corynebacterium glutamicum* with the ExeR gene inactivated through a gene expression enhancement technology.

The *Corynebacterium glutamicum* is ATCC31269.

A nucleotide sequence of the extracellular nuclease ExeR is shown in SEQ ID NO:1.

A nucleotide sequence of the adenosine triphosphate ATPase is shown in SEQ ID NO:2.

A method for constructing the recombinant *Corynebacterium glutamicum* mentioned above comprises the following steps of:

(1) carrying out PCR on the genome of the *Corynebacterium glutamicum* ATCC13032, and amplifying to obtain an upstream gene segment ExeR-R and a downstream gene segment ExeR-L of an ExeR gene knockout site, wherein nucleotide sequences of the upstream gene segment ExeR-R and the downstream gene segment ExeR-L are shown in SEQ ID NO:3 and SEQ ID NO:4 respectively;

(2) carrying out PCR on a knockout plasmid pJYS3_crtYf, and amplifying a crRNA sequence, specifically using a primer 5 and a primer 6 to replace an original recognition sequence on the plasmid with a 20 bp CRISPR-cpf1 recognition sequence selected at the ExeR gene knockout site to obtain an ExeR-1 with a nucleotide sequence shown in SEQ ID NO:5;

(3) cloning the ExeR-R and the ExeR-L obtained in the step (1) and the ExeR-1 obtained in the step (2) to the pJYS3_crtYf plasmid digested by ApaI/SwaI to obtain a knockout plasmid pJYS3_ExeR with a nucleotide sequence shown in SEQ ID NO:20;

(4) introducing the knockout plasmid pJYS3_ExeR obtained in the step (3) into the *Corynebacterium glutamicum* ATCC13032, and screening to obtain the *Corynebacterium glutamicum* with the ExeR gene knocked out; and verifying whether the gene knockout is in conformity with expectance by sequencing, wherein a sequencing service is provided by Suzhou GENEWIZ Biotech Co., Ltd; the knockout strain verified by sequencing is named ΔExeR strain; and a sequence after successful knockout of the ExeR gene is shown in SEQ ID NO:19;

(5) carrying out PCR on the genome of the *Corynebacterium glutamicum* ATCC13032, and amplifying an ATPase gene to obtain an amplified ATPase gene segment with a nucleotide sequence shown in SEQ ID NO:6;

(6) cloning the ATPase gene segment obtained in the step (5) to an overexpression plasmid pXMJ19 to obtain a recombinant plasmid pJYS3_ExeR with a nucleotide sequence shown in SEQ ID NO:21;

(7) introducing the recombinant plasmid obtained in the step (6) into the *Corynebacterium glutamicum* ΔExeR, and screening to obtain a recombinant *Corynebacterium glutamicum* ΔExeR+ATP simultaneously overexpressing the adenosine triphosphate ATPase while knocking out the extracellular nuclease ExeR.

In the step (1), sequences of primers designed to amplify the ExeR-R gene are as follows: a nucleotide sequence of a primer 1 is shown in SEQ ID NO:7; and a nucleotide sequence of a primer 2 is shown in SEQ ID NO:8; sequences of primers designed to amplify the ExeR-L gene are as follows: a nucleotide sequence of a primer 3 is shown in SEQ ID NO:9; and a nucleotide sequence of a primer 4 is shown in SEQ ID NO:10.

In the step (1), the PCR amplification method comprises: denaturating at 94° C. for 30 seconds, annealing at 55° C. for 30 seconds, extending at 72° C. for 1 minute, and repeating for 30 cycles.

In the step (2), sequences of primers designed to amplify the ExeR-1 gene are as follows: a nucleotide sequence of a primer 5 is shown in SEQ ID NO:11; and a nucleotide sequence of a primer 6 is shown in SEQ ID NO:12.

In the step (2), the PCR amplification method comprises: denaturating at 94° C. for 30 seconds, annealing at 55° C. for 30 seconds, extending at 72° C. for 10 seconds, and repeating for 30 cycles.

In the step (5), sequences of primers designed to amplify the ATPase gene are as follows: a nucleotide sequence of a primer 7 is shown in SEQ ID NO:13; and a nucleotide sequence of a primer 8 is shown in SEQ ID NO:14.

In the step (5), the PCR amplification method comprises: denaturating at 94° C. for 30 seconds, annealing at 55° C. for 30 seconds, extending at 72° C. for 1 minute, and repeating for 30 cycles.

In the step (6), the overexpression plasmid is pXMJ19.

A method for producing lysine by fermentation of the above-mentioned recombinant *Corynebacterium glutamicum* is also within the scope of protection of the present invention.

Preferably, the fermentation is immobilized fermentation, which comprises the following step of: fermenting the above-mentioned recombinant *Corynebacterium glutamicum* in a medium containing a solid carrier to obtain a lysine fermentation broth.

Specifically, the method comprises the following steps of:
(i) inoculating the recombinant *Corynebacterium glutamicum* into a seed medium, and culturing to obtain a seed solution; and
(ii) placing an immobilization carrier in a fermentation medium, inoculating the seed solution into the fermentation medium, and fermenting in batches to obtain a fermentation broth.

After each batch of fermentation, the obtained fermentation broth is replaced with a new fermentation medium for cultivation until sugar is exhausted, and the fermentation is finished to obtain the lysine after about 70 hours; wherein the sugar is a combination of glucose, molasses and sucrose.

In the step (i), concentrations of constituents in the seed medium are: 15 to 35 g/L sucrose, 5 to 15 g/L peptone, 1 to 10 g/L yeast powder, 5 to 10 g/L ammonium sulfate, 0.1 to 1 g/L magnesium sulfate heptahydrate, 1 to 5 g/L potassium dihydrogen phosphate, 5 to 15 g/L dipotassium hydrogen phosphate, and 1 to 5 g/L of urea; water is used as a solvent, and the culture is performed at 28 to 34° C. and 200 to 250 rpm for 10 to 14 hours.

In the step (ii), the immobilization carrier is any one or a combination of several of cotton fiber fabric, non-woven fabric, polyester fiber, polyvinyl alcohol fiber, zeolite, bacterial cellulose membrane, silk, bagasse, corn straw, activated carbon, plastic and glass. The immobilization carrier may be made into a sheet, a fiber, a mesh or a microsphere.

Preferably, the sheet immobilization carrier is pre-treated: the pre-treatment comprises cutting the immobilization carrier into a square of 2 to 8 cm×2 to 8 cm (preferably 5 cm×5 cm), washing with pure water, drying, soaking in ethanol for 1 hour, then washing with pure water, bathing in boiling water for 10 to 40 minutes (preferably 20 minutes), and drying; a dosage of the immobilization carrier is 1 to 100 g per 1 L fermentation medium.

In the step (ii), wherein concentrations of constituents in the fermentation medium are: 80 to 300 g/L glucose, 30 to 50 g/L ammonium sulfate, 0.5 to 1.5 g/L magnesium sulfate, 10 to 25 g/L molasses, 10 to 25 g/L corn steep liquor, 1 to 5 g/L potassium dihydrogen phosphate, 100 to 300 mg/L ferrous sulfate, 100 to 200 mg/L manganese sulfate, 40 to 80 mg/L nicotinamide, 5 to 15 mg/L calcium pantothenate, 5 to 15 mg/L VB1, 0.5 to 2 mg/L copper sulfate, 0.5 to 2 mg/L zinc sulfate, 0.5 to 2 mg/L biotin, and 10 to 50 g/L calcium carbonate, and water is used as a solvent.

In the step (ii), 50 mL fermentation medium was added to every 500 mL shake flask, and 10% to 30% (v/v) seed solution was inoculated, and fermented at 28 to 34° C. and 200 to 250 rpm/min for 60 to 90 hours (preferably 72 hours).

A metabolic pathway, a producing strain and fermentation conditions of the proline according to the application of the present invention are quite different from the lysine. The producing strain in the application of the present invention is ATCC31269, while the lysine producing strain in the prior art is ATCC13032. Moreover, compared with the lysine fermentation medium in the prior art, the fermentation medium in the application of the present invention is also different. In addition, the proline produced by glutamic acid fermentation is transformed by using the glutamic acid as a precursor, while the pathway to produce the lysine by fermentation is more complicated, and the precursors alpha-ketoglutaric acid and acetylcoenzyme A.

Beneficial effects: compared with the prior art, the present invention has the following advantages.

1. The present invention discloses the method for producing the lysine by the immobilized fermentation of the *Corynebacterium glutamicum*, which uses fibers (cotton fiber fabric, non-woven fabric, polyester fiber, polyvinyl alcohol fiber, bacterial cellulose membrane, silk, bagasse and corn straw) as immobilization materials, and the immobilized bacteria can be reused.

2. The present invention realizes continuous (or repeated batch fermentation) production of the lysine, and this is a manner that has not been realized in large-scale production at present.

3. The present invention constructs the *Corynebacterium glutamicum* simultaneously overexpressing the adenosine triphosphate ATPase while knocking out the extracellular nuclease ExeR, improves eDNA secretion of the *Corynebacterium glutamicum* and reduces eDNA degradation of the *Corynebacterium glutamicum*, so that a yield of continuous immobilized fermentation of the *Corynebacterium glutamicum* is increased by 49.67% than that of free fermentation of an original bacterium, and a fermentation cycle is shortened by 29.17%. A yield of bench scale can reach about 30 g/L.

DETAILED DESCRIPTION

Figure 1:
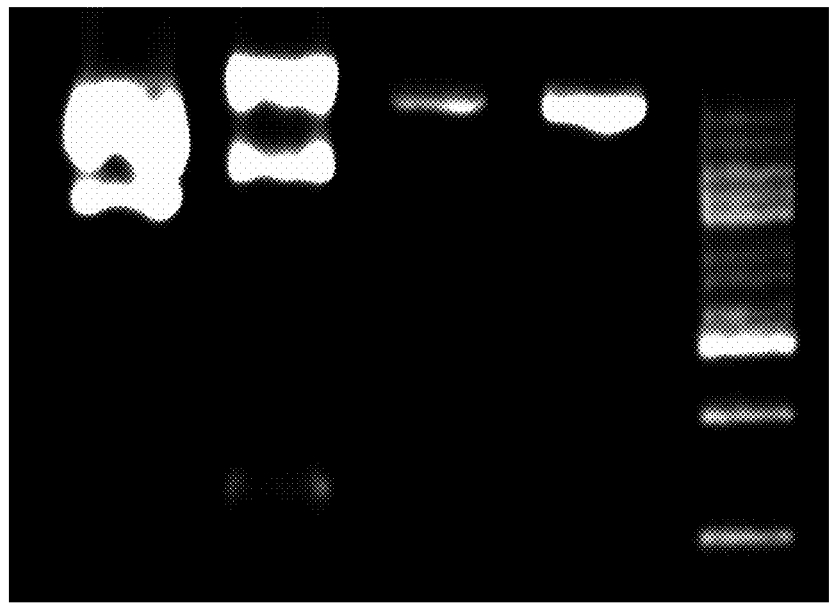
FIG. 1 is an agarose gel electrophoresis of pJYS3_ExeR and pXMJ19/*ATP plasmids. Lane 1 refers to an original plasmid pXMJ19, lane 2 refers to a recombinant plasmid pXMJ19/*ATP, lane 3 refers to pJYS3_crtYf, lane 4 refers to pJYS3_ExeR, and lane 5 refers to Marker. A size of the original plasmid pXMJ19 is 6601 bp, while a size of the recombinant plasmid pXMJ19/*ATP is 7741 bp. It can be seen from the figure that an ATPase gene segment is already inserted into the expression plasmid pXMJ19. A size of the Marker is 12000 bp.

The present invention may be better understood from the following embodiments. However, those skilled in the art will easily understand that the contents described in the embodiments are only used to illustrate the present invention, and should not and will not limit the present invention described in detail in the claims.

Plasmids pJYS3_crtYf and pXMJ19 used in the following embodiments were purchased from Wuhan MIAOLING Biotech Co., Ltd. Unless otherwise specified, all enzymes were purchased from TAKARA, plasmid extraction and gel recovery kits were purchased from TAKARA, and one-step cloning kits were purchased from Nanjing Vazyme Biotech Co., Ltd. The original *Corynebacterium glutamicum* strain (hereinafter abbreviated as original bacterium) for producing L-lysine was *Corynebacterium glutamicum* ATCC31269, which was purchased from American Type Culture Collection (ATCC) with a trade number ATCC31269.

Embodiment 1: Construct Extracellular Nuclease ExeR Knockout Plasmid

A chromosome of an original *Corynebacterium glutamicum* was used for performing PCR, and two gene fragments upstream and downstream an Exer gene knockout site, named ExeR-R and Exer-L, were amplified. Specifically, the PCR was carried out on the sequence ExeR-R by using the following primers 1 and 2 under the following reaction conditions: denaturating at 94° C. for 30 seconds, annealing at 55° C. for 30 seconds, extending at 72° C. for 1 minute, and repeating for 30 cycles. A gene segment (SEQ ID NO:3) of 1048 bp was amplified. The PCR was carried out on the sequence ExeR-L by using the following primers 3 and 4 under the following reaction conditions: denaturating at 94° C. for 30 seconds, annealing at 55° C. for 30 seconds, extending at 72° C. for 1 minute, and repeating for 30 cycles. A gene segment (SEQ ID NO:4) of 1035 bp was amplified.

A reaction system of the PCR amplification was as follows, a total system was µL (unless otherwise specified, all other PCR reactions were subject to this system).

| | |
|---|---|
| Buffer | 20 µL |
| dNTP | 10 µL |
| Template | 2 µL |
| Primer 1 | 2 µL |
| Primer 2 | 2 µL |
| PrimeSTAR | 2 µL |
| DdH$_2$O | 62 µL |

A plasmid pJYS3_crtYf was subjected to PCR, and a crRNA sequence was amplified. A primer 5 and a primer 6 were used to replace an original recognition sequence (SEQ ID NO:23) on the plasmid, i.e., a 21 bp CRISPR-cpf1 recognition sequence on a crtYf gene, with a 21 bp CRISPR-cpf1 recognition sequence (SEQ ID NO:22) selected at a knockout site of an ExeR genome, i.e., a 21 bp CRISPR-cpf1 recognition sequence on an ExeR gene. The replaced sequence was named ExeR-1. Specifically, the PCR was carried out on the sequence ExeR-1 by using the following primers 5 and 6 under the following reaction conditions:

denaturating at 94° C. for 30 seconds, annealing at 55° C. for 30 seconds, extending at 72° C. for 10 seconds, and repeating for 30 cycles. A gene segment (SEQ ID NO:5) of 110 bp was amplified.

The sequences ExeR-R, ExeR-L and ExeR-1 were cloned to a pJYS3_crtYf plasmid digested by ApaI/SwaI to obtain a knockout plasmid pJYS3_ExeR. An agarose gel electrophoresis was shown in FIG. 1. Lane 3 referred to an original pJYS3_crtYf plasmid, lane 4 referred to the constructed plasmid pJYS3_ExeR, and lane 5 referred to Marker. A size of the original pJYS3_crtYf plasmid was 11982 bp (SEQ ID NO:27), while a size of the recombinant plasmid pJYS3_ExeR was 11895 bp (SEQ ID NO:20).

The amplified ExeR-R sequence contained a 20 bp sequence homologous to the carrier and a 30 bp sequence homologous to the ExeR-L. In addition, the primer 1 had restriction enzyme recognition sites of ApaI. The amplified ExeR-L sequence contained a 30 bp sequence homologous to the ExeR-R and a 25 bp sequence homologous to the ExeR-L. The amplified ExeR-1 sequence contained a 25 bp sequence homologous to the ExeR-L and a 16 bp sequence homologous to the carrier. In addition, the primer 6 had restriction enzyme recognition sites of SwaI. The restriction enzyme recognition sites were marked in bold.

overexpressing the adenosine triphosphate ATPase. An agarose gel electrophoresis was shown in FIG. 1. Lane 1 referred to an original pXMJ19 plasmid, lane 2 referred to the constructed plasmid pXMJ19/*ATP, and lane 5 referred to Marker. A size of the original plasmid pXMJ19 was 6601 bp (SEQ ID NO:24), while a size of the recombinant plasmid pXMJ19/*ATP was 7741 bp (SEQ ID NO:21). It can be seen from the figure that an ATPase gene segment is already inserted into the expression plasmid pXMJ19.

Embodiment 3: Construct Strain Simultaneously Overexpressing Adenosine Triphosphate ATPase While Inactivating Extracellular Nuclease ExeR Gene The obtained pJYS3_ExeR recombinant plasmid was introduced into a competent cell of an original *Corynebacterium glutamicum*, and screened on an LB plate containing 25 ug/mL kanamycin. After culturing for 2 to 3 days, transformants were picked out, colony PCR was used to verify whether the ExeR gene on a genome was lost. A primer 9 and a primer 10 were used to carry out PCR on a genome of a knockout strain, a PCR product of an ExeR

TABLE 1

| | |
|---|---|
| Primer 1 | 5'~aagtagaacaactgttcaccgggcccacggaatcatctacc~3' (SEQ ID NO: 7) |
| Primer 2 | 5'~ggcgtgctggagtcggttccggcaggatta~3' (SEQ ID NO: 8) |
| Primer 3 | 5'~taatcctgccggaaccgactccagcacgcc~3' (SEQ ID NO: 9) |
| Primer 4 | 5'~tgagctagctgtcaatctagagcgtcgaattcggt~3' (SEQ ID NO: 10) |
| Primer 5 | 5'~acgctctagattgacagctagctca~3' (SEQ ID NO: 11) |
| Primer 6 | 5'~ctgagcctttcgttttatttaaatgtaacgctccaaccgtcgaggatctacaacagtaga~3' (SEQ ID NO: 12) |

Embodiment 2: Construct Adenosine Triphosphate ATPase Overexpression Plasmid

A chromosome of an original *Corynebacterium glutamicum* was used for PCR, and an ATPase gene was amplified.

Specifically, the PCR was carried out by using the following primers 7 and 8 under the following reaction conditions: denaturating at 94° C. for 30 seconds, annealing at 55° C. for 30 seconds, extending at 72° C. for 1 minute, and repeating for 30 cycles. A gene segment (SEQ ID NO:6) of 1186 bp was amplified.

The amplified sequence contained an ATPase coding sequence and a 20 bp sequence homologous to the carrier. In addition, the primer 7 had restriction enzyme recognition sites of BamHI, and the primer 8 had restriction enzyme recognition sites of BamHI. The restriction enzyme recognition sites of the BamHI were marked in bold.

TABLE 2

| | |
|---|---|
| Primer 7 | 5'~gcctgcaggtcgactctagaggatccatgactgacattgatctggt~3' (SEQ ID NO: 13) |
| Primer 8 | 5'~aattcgagctcggtacccggggatccctagggcataaaccatgcct~3' (SEQ ID NO: 14) |

Figure 2:
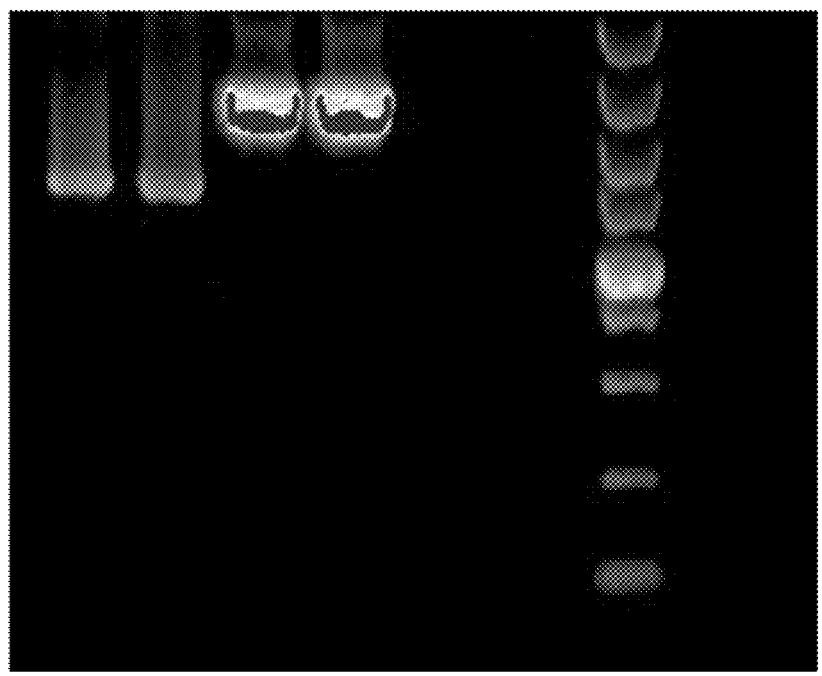
FIG. 2 is a PCR agarose gel electrophoresis of ExeR genes on genomes of a ΔExeR strain and an original strain. Lanes 1 and 2 refer to PCR products of the ExeR gene on the genome of the ΔExeR strain, lanes 3 and 4 refer to PCR products of the ExeR gene on the genome of the original strain, and lane 5 refers to Marker. A primer 9 and a primer 10 are used to carry out PCR on a genome of a knockout strain, a PCR product of an ExeR gene on a successfully knocked out genome of a mutant strain is 1494 bp, while that of a control wild strain is 2619 bp. A size of the Marker is 5000 bp.

The obtained polynucleotide and the pXMJ19 plasmid treated by the restriction enzyme BamHI were cloned in one step to obtain a recombinant plasmid pXMJ19/*ATP for gene on a successfully knocked out genome of a mutant strain was 1494 bp (SEQ ID NO:25), while that of a control wild strain was 2619 bp (SEQ ID NO:26). An agarose gel electrophoresis was shown in FIG. 2. Lanes 1 and 2 referred to PCR products of the ExeR gene on the genome of the mutant strain, lanes 3 and 4 referred to PCR products of the control wild strain, and lane 5 referred to Marker. The ExeR gene on the genome of the original *Corynebacterium glutamicum* was finally verified by sequencing, wherein a sequencing service was provided by Suzhou GENEWIZ Biotech Co., Ltd. The obtained strain with the extracellular nuclease ExeR gene inactivated was named ΔExeR strain, and a sequence of successfully knocking out the ExeR gene was shown in SEQ ID NO:19.

The obtained pXMJ19/*ATP recombinant plasmid was introduced into a competent cell of the ΔExeR strain, and screened on an LB plate containing 6.5 ug/mL chloramphenicol. After culturing for 2 to 3 days, transformants were picked out, and then colony PCR verification was carried out, to obtain the recombinant strain simultaneously overexpressing the adenosine triphosphate ATPase while knocking out the extracellular nuclease ExeR gene, which was named ΔExeR+ATP strain, namely, the recombinant bacteria of the patent. A primer 11 and a primer 12 were used to carry out PCR, to verify whether the gene was inserted into the recombinant plasmid.

TABLE 3

| Primer 9 | 5'~gtgagaccaaaggtgaactg~3'<br>(SEQ ID NO: 15) |
|---|---|
| Primer 10 | 5'~gtaggttctgcaggatcagt~3'<br>(SEQ ID NO: 16) |
| Primer 11 | 5'~ggaattgtgagcggataaca~3'<br>(SEQ ID NO: 17) |
| Primer 12 | 5'~gtatcaggctgaaaatcttc~3'<br>(SEQ ID NO: 18) |

Figure 3:
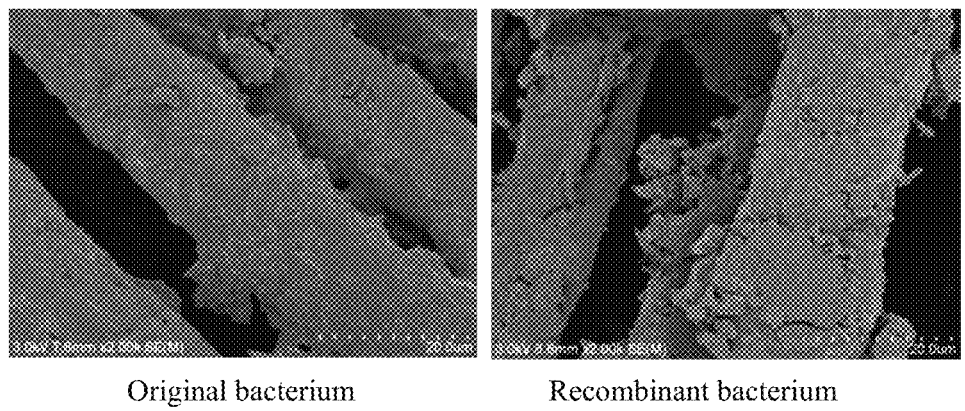
FIG. 3 is an electron micrograph of an original *Corynebacterium glutamicum* and a recombinant *Corynebacterium glutamicum*.
Figure 5:
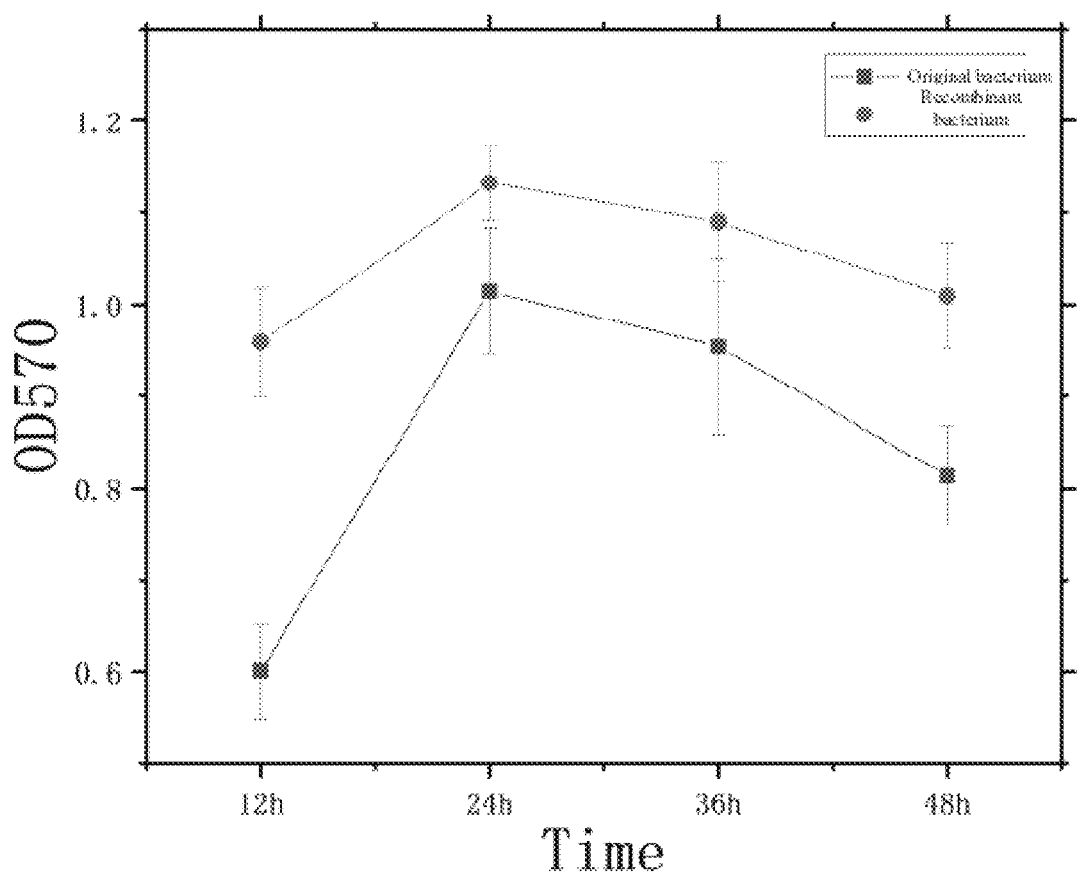
FIG. 5 is experimental data of semi-quantitative measurement of biofilm quantity of an original *Corynebacterium glutamicum* and a recombinant *Corynebacterium glutamicum* by crystal violet staining

96-well plate and SEM experiments were carried out on the modified strain was successfully constructed. Data of the 96-well plate experiment was shown in FIG. 5. It can be seen that a biomass of the recombinant bacterium is increased by 59% than that of the original bacterium in 12 hours, while a biomass difference is gradually narrowed as the strain continues to grow. An electron micrograph was shown in FIG. 3. It can be seen intuitively and concretely that a biofilm of the recombinant bacterium is thicker than that of the original bacterium, forming a block, while the biofilm of the original bacterium is thinner. Continuous immobilized fermentation was carried out after a film forming effect was improved.

Embodiment 4: Production of Lysine by Immobilized Fermentation of Recombinant Bacterium on Different Carriers An activation medium was composed of: 10 g/L glucose, 10 g/L peptone, 5 g/L yeast powder and 10 g/L sodium chloride.

A seed medium was composed of: 25 g/L sucrose, 10 g/L peptone, 5 g/L yeast powder, 5 g/L ammonium sulfate, 1 g/L magnesium sulfate heptahydrate, 5 g/L potassium dihydrogen phosphate, 12 g/L dipotassium hydrogen phosphate and 5 g/L urea.

A formula of a fermentation medium comprised: 100 g/L glucose, 40 g/L ammonium sulfate, 1 g/L magnesium sulfate, 20 g/L molasses, 20 g/L corn steep liquor, 1 g/L potassium dihydrogen phosphate, 150 mg/L ferrous sulfate, 100 mg/L manganese sulfate, 50 mg/L nicotinamide, 10 mg/L calcium pantothenate, 10 mg/L VB1, 1 mg/L copper sulfate, 1 mg/L zinc sulfate, 2 mg/L biotin, and 40 g/L calcium carbonate.

5 mL activation culture medium was added into every 50 mL centrifuge tube, inoculated with the recombinant bacterium prepared in Embodiment 3, and activated at 30° C. and 220 rpm for 20 hours.

After activation, the mixture was poured into 500 mL shake flask filled with 50 mL seed medium, and cultured at 30° C. and 220 rpm for 12 hours.

50 mL fermentation medium was poured into every 500 mL shake flask, and a carrier shown in Table 4 was also put into the fermentation medium for sterilization together at 115° C. for 15 minutes. Preferably, a dosage of the carrier was 30 g/L.

5 mL seed solution was inoculated to the fermentation medium, and fermented at 30° C. and 220 rpm for 72 hours.

Continuous immobilized fermentation: during fermentation, the bacterium was already adsorbed on the immobilization carrier in a first batch; at the moment, the shake flask cultivation had passed for about 72 hours; in a second batch, a fermentation broth was dumped, the immobilization carrier adsorbed with the bacterium was left, and then 50 mL new fermentation medium was poured into the shake flask for cultivation until sugar was exhausted, which lasted for about 60 hours, wherein the carbohydrate was a combination of glucose, molasses and sucrose. Data of a fermentation cycle and a yield of the lysine were measured. This method was adopted in continuous immobilized fermentation in subsequent batches. Data of the continuous fermentation in the last ten batches was shown in Table 4.

TABLE 4

Continuous immobilized fermentation (immobilization of recombinant bacterium) of different carriers in 10 batches

| Immobilization materials | Mean fermentation cycle (h) | Mean yield (g/L) of lysine |
|---|---|---|
| Cotton fiber fabric | 51 | 30.15 |
| Non-woven fabric | 59 | 25.51 |
| Polyester fiber | 53 | 28.17 |
| Polyvinyl alcohol fiber | 54 | 26.78 |
| Zeolite | 72 | 19.80 |
| Bacterial cellulose membrane | 68 | 24.21 |
| Silk | 70 | 21.56 |
| Bagasse | 69 | 22.84 |
| Corn straw | 71 | 26.59 |
| Activated carbon | 68 | 28.89 |
| Plastic | 72 | 21.65 |
| Glass | 72 | 20.54 |

It can be seen from Table 4 that the cotton fiber is most conducive to the continuous immobilized fermentation, so the cotton fiber was used as an immobilization carrier in the subsequent continuous immobilized fermentation.

Embodiment 5: Lysine Fermentation Experiment of Recombinant Bacterium (Immobilization of Recombinant Bacterium on Cotton Fiber Carrier)

An activation medium was composed of: 10 g/L glucose, 10 g/L peptone, 5 g/L yeast powder and 10 g/L sodium chloride.

A seed medium was composed of: 25 g/L sucrose, 10 g/L peptone, 5 g/L yeast powder, 5 g/L ammonium sulfate, 1 g/L magnesium sulfate heptahydrate, 5 g/L potassium dihydrogen phosphate, 12 g/L dipotassium hydrogen phosphate and 5 g/L urea.

A formula of a fermentation medium comprised: 100 g/L glucose, 40 g/L ammonium sulfate, 1 g/L magnesium sulfate, 20 g/L molasses, 20 g/L corn steep liquor, 1 g/L potassium dihydrogen phosphate, 150 mg/L ferrous sulfate, 100 mg/L manganese sulfate, 50 mg/L nicotinamide, 10 mg/L calcium pantothenate, 10 mg/L VB1, 1 mg/L copper sulfate, 1 mg/L zinc sulfate, 2 mg/L biotin, and 40 g/L calcium carbonate. 5 mL activation culture medium was added into every 50 mL centrifuge tube, inoculated with the recombinant bacterium prepared in Embodiment 3, and activated at 30° C. and 220 rpm for 20 hours.

After activation, the mixture was poured into 500 mL shake flask filled with 50 mL seed medium, and cultured at 30° C. and 220 rpm for 12 hours.

50 mL fermentation medium was poured into every 500 mL shake flask, and a pro-treated cotton fiber carrier was also put into the fermentation medium for sterilization together at 115° C. for 15 minutes.

5 mL seed solution was inoculated to the fermentation medium, and fermented at 30° C. and 220 rpm for 72 hours.

Figure 6:
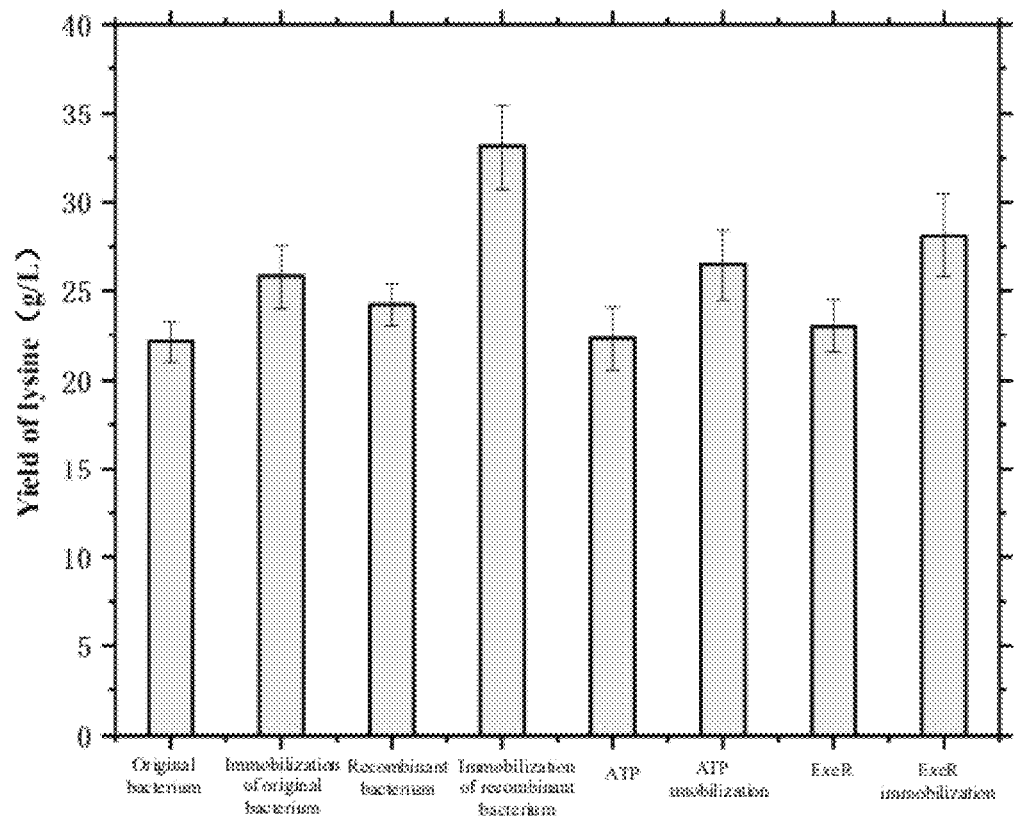
FIG. 6 is a comparison diagram of yields of lysine by immobilized fermentation and free fermentation of an original *Corynebacterium glutamicum*, a recombinant *Corynebacterium glutamicum*, an ATP strain and a ΔExeR strain.

Continuous immobilized fermentation: during fermentation, the bacterium was already adsorbed on the immobilization carrier in a first batch; at the moment, the shake flask cultivation had passed for about 72 hours; in a second batch, a fermentation broth was dumped, the immobilization carrier adsorbed with the bacterium was left, and then 50 mL new fermentation medium was poured into the shake flask for cultivation until sugar is exhausted, which lasted for about 60 hours, wherein the sugar was a combination of glucose, molasses and sucrose. Data of a fermentation cycle measured was shown in FIG. 4. A yield of the lysine was shown in FIG. 6. This method was adopted in continuous immobilized fermentation in subsequent batches.

Pre-treatment of cotton fiber carrier material: a cotton fiber carrier was cut into a square of 5 cm×5 cm, washed with pure water, dried, soaked in ethanol for 1 hour, then washed twice with pure water, bathed in boiling water for 20 minutes, put into an oven for drying, weighed to be 1.5 g, and then put into a shake flask filled with the fermentation broth for sterilization together at 115° C. for 15 minutes.

Comparative Example 1: Immobilization (Original Bacterium) of Original Bacterium The recombinant bacterium inoculated in Embodiment 5 was replaced with an original bacterium, and other steps were the same as those in Embodiment 5. Data of a fermentation cycle measured was shown in FIG. 4. A yield of the lysine was shown in FIG. 6.

Comparative Example 2: Free Fermentation (Recombinant Bacterium) of Recombinant Bacterium No carrier was added into a fermentation medium, and other steps were the same as those in Embodiment 5. Data of a fermentation cycle measured was shown in FIG. 4. A yield of the lysine was shown in FIG. 6.

Comparative Example 3: Free Fermentation (Original Bacterium) of Original Bacterium The recombinant bacterium inoculated in Embodiment 5 was replaced with an original bacterium, no carrier was added into a fermentation medium and, and other steps were the same as those in Embodiment 5. Data of a fermentation cycle measured was shown in FIG. 4. A yield of the lysine was shown in FIG. 6.

Figure 4:
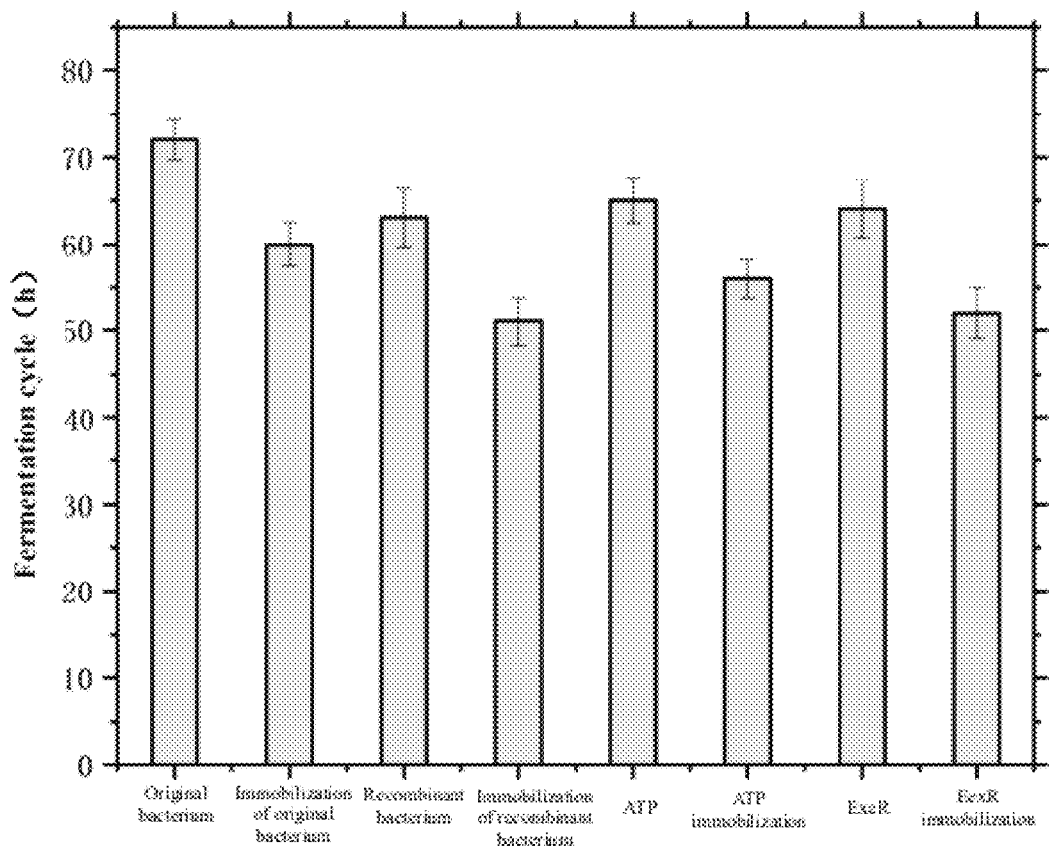
FIG. 4 is a cycle diagram of immobilized fermentation and free fermentation of an original *Corynebacterium glutamicum*, a recombinant *Corynebacterium glutamicum*, an ATP strain and a ΔExeR strain.

It can be seen from FIG. 4 that compared with the free fermentation, cycles of the immobilized fermentations are all shortened, wherein an immobilized fermentation cycle of the recombinant bacterium is shortened by 29.17% than that of the original bacterium. It can be seen from FIG. 6 that compared with free fermentation, the yield of the lysine obtained by the immobilized fermentation is improved, and the immobilized yield of the recombinant bacterium is 49.67% higher than that of the original bacterium. The shortening of the fermentation cycle and the improvement of the yield of the lysine above are all due to the use of the immobilized fermentation and the recombinant bacterium to enhance a film-forming ability of the *Corynebacterium glutamicum*.

Comparative Example 4: Construct Strain with Inactivated Exer Gene in *Corynebacterium glutamicum*

The obtained pJYS3_ExeR recombinant plasmid was introduced into a competent cell of an original *Corynebacterium glutamicum*, and screened on an LB plate containing 25 ug/mL kanamycin. After culturing for 2 to 3 days, transformants were picked out, colony PCR was used to verify whether the ExeR gene on a genome was lost. A primer 9 and a primer 10 were used to carry out PCR on a genome of a knockout strain, a PCR product of an ExeR gene on a successfully knocked out genome of a mutant strain was 1494 bp (SEQ ID NO:25), while that of a control wild strain was 2619 bp (SEQ ID NO:26). An agarose gel electrophoresis was shown in FIG. 2. Lanes 1 and 2 referred to PCR products of the ExeR gene on the genome of the mutant strain, lanes 3 and 4 referred to PCR products of the control wild strain, and lane 5 referred to Marker. The ExeR gene on the genome of the original *Corynebacterium glutamicum* was finally verified by sequencing, wherein a sequencing service was provided by Suzhou GENEWIZ Biotech Co., Ltd. The obtained strain with the extracellular nuclease ExeR gene inactivated was named ΔExeR strain.

Comparative Example 5: Construct Strain Overexpressing Adenosine Triphosphate Atpase in *Corynebacterium glutamicum*

The obtained pXMJ19/*ATP recombinant plasmid was introduced into a competent cell of an original *Corynebacterium glutamicum*, and screened on an LB plate containing 6.5 ug/mL chloramphenicol. After culturing for 2 to 3 days, transformants were picked out, and then colony PCR verification was carried out, to obtain a recombinant strain simultaneously overexpressing the adenosine triphosphate ATPase, which was named ATP strain.

Comparative Example 6: Immobilized Fermentation of ΔExeR Strain

The recombinant bacterium inoculated in Embodiment 5 was replaced with a ΔExeR strain (knocking out an ExeR gene in an original *Corynebacterium glutamicum*), and other steps were the same as those in Embodiment 5. Data of a fermentation cycle measured was shown in FIG. 4. A yield of the lysine was shown in FIG. 6.

Comparative Example 7: Immobilized Fermentation of Atp Strain

The recombinant bacterium inoculated in Embodiment 5 was replaced with an ATP strain (overexpressing an ATPase gene in an original *Corynebacterium glutamicum*), and other steps were the same as those in Embodiment 5. Data of a fermentation cycle measured was shown in FIG. 4. A yield of the lysine was shown in FIG. 6.

By comparing the fermentation data of the original bacterium, the recombinant bacterium, the ΔExeR strain and the ATP strain, it can be seen that knocking out the ExeR gene alone or overexpressing the ATPase gene alone can improve a fermentation yield and shorten a fermentation cycle, and, in terms of the yield of the lysine, an effect of knocking out the ExeR gene alone is slightly better than overexpressing the ATPase gene alone in terms of the yield of the lysine. It can be known from FIG. 6 that the yield of the lysine by the immobilized fermentation of the ATP strain is increased by 2.56% than that of the immobilized fermentation of the original bacterium, the yield of the lysine by the immobilized fermentation of the ΔExeR strain is increased by 9.00% than that of the immobilized fermentation of the original bacterium, while the yield of the lysine by the immobilized fermentation of the recombinant bacterium is increased by 28.54% than that of the immobilized fermentation of the original bacterium. In conclusion, in terms of the yield of the lysine, the recombinant bacterium has the best fermentation performance.

Embodiment 6: Determination Method of Reducing Sugar

DNS (dinitrosalicylic acid) was used to carry out a redox reaction with reducing sugar in an alkaline condition to produce 3-amino-5-nitrosalicylic acid. The product was brown-red when boiled, and a color of the product was proportional to a content of the reducing sugar in a certain concentration range. The content of the reducing sugar was determined by a ultraviolet spectrophotometer ($OD_{540}$).

A sample was properly diluted to an estimated sugar content ranging from 0.1 mg/mL to 1.0 mg/mL. 0.5 mL diluted sample was added into a 10 mL graduated test tube, and then 0.5 mL DNS was added. The mixture was boiled in boiling water for 5 minutes, and then immediately cooled for 5 minutes. 8 mL pure water was added in the mixture to blend. Moreover, 0.5 mL pure water and 0.5 mL DNS sample were set as blank samples. A standard content curve of the DNS reducing sugar used in this experiment was prepared in advance, and an absorption value was detected by an ultraviolet spectrophotometer at 540 nm and used as a magnitude of the content of the reducing sugar.

Embodiment 7: Determination of Content of Lysine

100 μL fermentation broth was sampled from each flask and diluted 50 times with 0.1 M hydrochloric acid solution, then 400 μL diluent was taken from each sample, followed by PITC precolumn derivatization. A content of the lysine was detected by an RP-HPLC method, and a concentration of the lysine in each sample was calculated.

Continuous immobilized fermentation experiments were performed with an original bacterium and the recombinant bacterium constructed by the present invention. 10 batches of fermentation experiments were performed, and fermentation results were shown in Table 5. It can be seen from FIG. 6 that the yield of the lysine of the modified bacterium subjected to the continuous immobilized fermentation is 49.67% higher than that of the original bacterium subjected to the free fermentation. It can be seen from FIG. 4 that the immobilized fermentation cycle of the modified bacterium is shortened by 29.17% than that of the original bacterium.

Embodiment 8: Semi-Quantitative Measurement of Biofilm Quantity by Crystal Violet Staining 200 uL fermentation medium (without immobilization carrier and calcium carbonate) was added into a colorless 96-well plate, and then 20 uL original bacterium and recombinant bacterium were added respectively. After culturing for 12 hours, 24 hours, 36 hours and 48 hours, and then, OD values at 570 nm were measured by crystal violet staining method and a microplate reader. It can be seen from FIG. 5 that a film-forming ability of the recombinant bacterium simultaneously overexpressing an adenosine triphosphate ATPase while knocking out an extracellular nuclease ExeR is obviously improved.

The present invention provides the *Corynebacterium glutamicum* simultaneously overexpressing the adenosine triphosphate ATPase while knocking out the extracellular nuclease ExeR and the constructing method thereof as well as the application ideas and methods in producing the lysine. There are many methods and ways to realize the technical solutions. The above is only the preferred embodiments of the present invention. It should be pointed out that those of ordinary skills in the art can make some improvements and embellishments without departing from the principle of the present invention, and these improvements and embellishments should also be regarded as falling with the scope of protection of the present invention. All the unspecified components in the embodiments can be realized by the prior art.

REFERENCES TO THE SEQUENCE LISTING

Applicant hereby makes reference to the sequence listing that is submitted in electronic format. The Sequence Listing is provided as a file entitled 49374_SEQLIST.txt, created on Feb. 4, 2021 which is 71,454 bytes in size. The information in the electronic format of the sequence listing is incorporated herein by reference in its entirety.

TABLE 5

Yield of lysine (g/L) of immobilized bacterium subjected to continuous fermentation in 10 batches

| Batch | First | Second | Third | Fourth | Fifth | Sixth | Seventh | Eighth | Ninth | Tenth |
|---|---|---|---|---|---|---|---|---|---|---|
| Immobilization of original bacterium | 25.79 | 25.18 | 25.73 | 26.12 | 25.47 | 25.91 | 26.55 | 26.01 | 27.51 | 26.37 |
| Immobilization of recombinant bacterium | 32.18 | 32.84 | 33.16 | 33.34 | 31.92 | 33.85 | 32.86 | 33.71 | 33.89 | 33.75 |

The invention claimed is:

1. A method for producing lysine, comprising utilizing fermentation of a recombinant *Corynebacterium glutamicum*, wherein
an extracellular nuclease ExeR of the recombinant *Corynebacterium glutamicum* is inactivated, and meanwhile, expression of an adenosine triphosphate ATPase is enhanced,
a nucleotide sequence of the extracellular nuclease ExeR is shown in SEQ ID NO:1, and
a nucleotide sequence of the adenosine triphosphate ATPase is shown in SEQ ID NO:2.

2. The method according to claim 1, wherein the fermentation is immobilized fermentation.

3. The method according to claim 2, wherein the recombinant *Corynebacterium glutamicum* is fermented in a medium containing a solid carrier to obtain a lysine fermentation broth.

4. The method according to claim 3, wherein the solid carrier is any one or a combination of several of cotton fiber fabric, non-woven fabric, polyester fiber, polyvinyl alcohol fiber, zeolite, bacterial cellulose membrane, silk, bagasse, corn straw, activated carbon, plastic and glass.

5. The method according to claim 3, wherein a dosage of the solid carrier in the fermentation medium is 1 to 100 g/L.

6. The method according to claim 3, wherein concentrations of constituents in the medium are: 80 to 300 g/L glucose, 30 to 50 g/L ammonium sulfate, 0.5 to 1.5 g/L magnesium sulfate, 10 to 25 g/L molasses, 10 to 25 g/L corn steep liquor, 1 to 5 g/L potassium dihydrogen phosphate, 100 to 300 mg/L ferrous sulfate, 100 to 200 mg/L manganese sulfate, 40 to 80 mg/L nicotinamide, 5 to 15 mg/L calcium pantothenate, 5 to 15 mg/L VB1, 0.5 to 2 mg/L copper sulfate, 0.5 to 2 mg/L zinc sulfate, 0.5 to 2 mg/L biotin, and 10 to 50 g/L calcium carbonate, and water is used as a solvent.

7. The method according to claim 3, wherein, after each batch of fermentation, the obtained fermentation broth is replaced with a new fermentation medium for cultivation until sugar is exhausted to obtain the lysine fermentation broth.

8. The method according to claim 3, wherein the fermentation is performed at 28 to 34° C. and 200 to 250 rpm for 20 to 90 hours.

* * * * *

SEQUENCE LISTING

<160> NUMBER OF SEQ ID NOS: 27

<210> SEQ ID NO 1
<211> LENGTH: 2751
<212> TYPE: DNA
<213> ORGANISM: Corynebacterium glutamicum

<400> SEQUENCE: 1

| | | | | | |
|---|---|---|---|---|---|
| atgtctcgca | tttctgcgcg | cactctggca | atcgcacttg | ccggtgcaac | cgcggccagc | 60 |
| ctggcagttg | ttccagcagc | aacagctaat | cctgccggaa | ccgctcctgt | catcaacgaa | 120 |
| atctacggag | gcggtggaaa | cagcggatcg | ttgttctcca | acgacttcat | tgagctctac | 180 |
| aacccaacct | caggggacat | ttccctcgac | ggttggagcg | ttacctacta | cgcagccaac | 240 |
| ggtaactccg | gcggaaccac | aaacctgacc | ggaaacatcc | ctgccaacgg | ttactacctc | 300 |
| atccagcaac | gcgcaggcag | caacaacacc | ggcgctctgc | ctaccccaga | cgccaccggt | 360 |
| aacttggcaa | tgggtgcctc | ccaaggatca | gttgcactga | ccgacaactc | tggcctaacc | 420 |
| gctgaccttg | tcggattcgg | tggcacgtcc | atgtttgaag | aacagctgc | tgcacctgag | 480 |
| accagcaaca | aattgtctgt | tcaacgcaaa | gaagttggcg | ctgactctga | taacaactcc | 540 |
| gtagacttcg | agactggagc | tccaactcca | acgtcctcgg | gaggatccgc | tcctgttgac | 600 |
| ccaggcgagc | cagaaactcc | agtaaaccct | ggggaaacag | tctccatcgc | acaaatccaa | 660 |
| ggaaccggtc | tcgctacccc | actcgagggt | cagaccgtca | ccaccgaagg | tattgtcact | 720 |
| gccgtttacg | cagaaggtgg | cttcaacggt | tactacatcc | agacacctgg | atctggtact | 780 |
| gcaccaaagg | ttgctggcga | cgcatccgac | ggcatcttcg | tctacgtggg | aagcaatggt | 840 |
| tcctacccag | agctcggcgc | atctgtcacc | gtcactggca | aggccaccga | acactacgag | 900 |
| atgactcagc | taggcaactc | ctccttcacc | gtttcggaca | ccgcattcga | gccagtaacc | 960 |
| ccactcgaac | tggacaccgt | tcctactggc | gatgacattc | gcgaagcata | cgaaggcatg | 1020 |
| ctgctgaagc | caaccggcgc | tcacaccgtg | accaacaact | acgcaaccaa | caccttcggt | 1080 |
| gaaattgccc | tcgccccagg | taacgagcct | ttgtaccagg | ccactcaaat | ggtggcaccg | 1140 |
| ggagccgaag | cgattgcgta | cgaggcggaa | aacgtcgcaa | agcaaattac | gctggatgac | 1200 |
| ggacgctccg | gcaactacac | tcgcggcgac | tccagcacgc | ctatggcatg | gcttgtgcag | 1260 |
| gacggtggcg | agaccatcaa | gtccatccgc | accggcgacc | aggtggaatt | ccaggcacca | 1320 |
| gtaatcttcg | attaccgcta | cgacctgtgg | aaattccagc | caaccacccc | tgtcaccggc | 1380 |
| aacaccgcaa | gctccgacct | tcctatcacc | tgggatgaca | cccgcgcggc | tgagctagct | 1440 |
| tcaatcaatg | acgttgctgg | cgaattccac | atcgcaagct | tcaacgtgct | caactacttc | 1500 |
| acctctctcg | gcgaagatga | accaggctgc | agcgcataca | gggatatcaa | caacacccca | 1560 |
| gtcaccgcca | caactgtaa | cgtccgtggc | gcttacaccg | aagaagcact | cgaagatcag | 1620 |
| cagagcaaga | tcgtcgaagc | aatcaaccgc | cttgacgtcg | atgttcttgg | acttgaagaa | 1680 |
| atcgaaaaca | ccgcgaccgt | caccggcgac | gtctcccgtc | gcgatgacgc | actcaatacc | 1740 |
| ctcgtcgcag | cactcaacga | agcagttgga | tccgatcgct | gggcggccgt | cgaatctcca | 1800 |
| gaacaattgg | gcaccgatga | agactacatc | cgcgtcgcct | tcatctacga | ccaaaccacc | 1860 |
| gtcaagcccg | tcggcgaatc | ccgaatcttc | gacgacgcag | ccttcaccgg | caccgcacgc | 1920 |
| cagccactcg | cacaggaatt | ccagccactc | aacgacagcg | agaaatcctt | cgtcggcgta | 1980 |
| gtcaaccact | tcaagtccaa | gggctctgtc | actcgtggag | acgccgacac | cggcgacggc | 2040 |
| caaggcaaca | acgccaacgt | tcgcgtcgca | caggcacagg | cactcatcga | ccacctggaa | 2100 |

| | | |
|---|---|---|
| aaccaggacg actgggcatc caagccaatc ttcatcctcg gcgacaccaa ctcctacgcc | 2160 | |
| aaggaaaccg cgatgaccac cctttacggc gctggctaca ccaacatcgc caccgaattc | 2220 | |
| gacgctggct acagctacca gttctccggc cgcattggca gcctcgacca cgcactcggc | 2280 | |
| aacgaagcag ccatgaagca cgtcatcgac gccgaggtct gggacatcaa cgctgacgaa | 2340 | |
| gcaatcgcat tcgaatactc ccgtcgactc aacaacacct ccgacgtatt cgagaacaac | 2400 | |
| gtcttccgct cctccgacca cgacccgatc aaggtcggat caacctcag cgagaccact | 2460 | |
| gagcccacca ttccggtaga gcccactgat cctgcagaac ctaccgatcc aactacccca | 2520 | |
| gttaagccaa ctgatccggt agagaccacg gatccatctg agccaaccga ccctgcagaa | 2580 | |
| cctactgatc cagctgaacc aactgaccct gaggaaacga agaagccaga ggagccgaag | 2640 | |
| aaccctggtt cctccaacgg aagctcccaa tacgccacca ttgcagcaat catcgcagca | 2700 | |
| atcctaggtg ccattgcttt ggccttccag ttcttcccat tcaagttcta a | 2751 | |

<210> SEQ ID NO 2
<211> LENGTH: 1134
<212> TYPE: DNA
<213> ORGANISM: Corynebacterium glutamicum

<400> SEQUENCE: 2

| | | |
|---|---|---|
| atgactgaca ttgatctggt ggtggaaaac gtccaaagga ttatcgccac caaagagaca | 60 | |
| ccgccgacct ctgcggaaat agcgagcctg attcggaac aagcaggcgt gatcagtaac | 120 | |
| gaggacatcg tgatggtgtt gcgtcgactg cgcagtgatt ctgtgggcgt gggaccgttg | 180 | |
| gaatctctgc ttgcgcttcc tggcgtgacg gatgtgttgg ttaatgccca tgacagcgtg | 240 | |
| tggattgatc gcggtcaggg cgtggagaaa gtcgacatgg atctgggctc agaggaggcg | 300 | |
| gtgcgtcgcc ttgccacccg gttggcgttg acctgtggca gacgcttaga tgatgcgcag | 360 | |
| ccttcgctg atggccgaat caccagggac gacggcagcg tgttgcgcat tcacgcggtg | 420 | |
| ttggcaccct tggcggaatc cggcacgtgc atcagtgtgc gagtactgcg tcaagcacgg | 480 | |
| ctgagccttg atgatcttat ccaaagcggc acggtgcctg aggacatcgc gcctgcgctc | 540 | |
| cggaacatca tcaatcaacg cgctcgttc cttgttgtcg gtggcaccgg cacagggaaa | 600 | |
| accacattgc tgtccgcgat gctcaccgaa gttccgctg atcaacgaat catctgcatc | 660 | |
| gaggacaccg cagagcttca tcccggccat ccaagcacca tcaacttggt gtctcgccaa | 720 | |
| gcaaacgtcg agggcgccgg cgccgtgagc atggcggatt tgttgaaaca atcgctgcgc | 780 | |
| atgaggcctg accggattgt cgtcggagag attcgcggtg cggaagtcgt ggatcttttg | 840 | |
| gctgcgatga ataccggaca cgacggcggt gctggcacca ttcacgcgaa ctccatctct | 900 | |
| gaagttcccg cgcgcatgga agctcttgcg gcgaccggcg gattggaccg catggcattg | 960 | |
| cattctcaac tcgcggccgc agtggacatt gtgctggtca tgaaacacac ccctttggc | 1020 | |
| cgcaggctag ctcaactcgg ggtgctccgc ggaaatcctg tgaccacgca ggtggtgtgg | 1080 | |
| gatttggacc acggcatgca cgaagggagc gaagaggcat ggtttatgcc ctag | 1134 | |

<210> SEQ ID NO 3
<211> LENGTH: 1048
<212> TYPE: DNA
<213> ORGANISM: Corynebacterium glutamicum

<400> SEQUENCE: 3

| | | |
|---|---|---|
| aagtagaaca actgttcacc gggcccacgg aatcatctac ctcaagctcg aagcgctttc | 60 | |
| cctgacggac atcggaaacg ccagaaactc cgatacgtcc gagggcgcgg tgtaccgcct | 120 | |

```
gcccctgggg atccagaatc tcagccttag gcatgacatt gacaactaca cgggccacgg      180
tattttccct tactcaagaa atggggagga caatgtttta cgagcacaag tgtaactgtt      240
gccactggtc aaacctagcc agcccttaga tagggagatt ctcctcgatt gcttccacta      300
cctcagctgc agatggttcc gtccgaggag caaagcgctt aatcgtatta ccttctgcat      360
ctaccaggaa tttctcaaaa ttccactcga tttcgctacc atcagttgcc tctttgagca      420
ccttgtacag ggggtgggca ccctccccat tcacctcggt tttgctcaag agcgggaagg      480
tgacgtcgta ctgattttgc gcgaaagcac acacctcagc gtcggttcca ggttcctggc      540
cgttgaattg attgcagggc acgccaatga caaagaagcc tcgatcttgg tattcctcat      600 acagttttttg aagcccttca tactgtggcg tgagtccgca cttggatgcc acgttcacga      660
tgagcaaaag gtggcccgcc caatccgcca tggtggtttc tgtgccgtcg ttgagagtta      720
cgctgatgtc atgaatagaa gtcataatcg caaccctagt tgaggggggag gatttagtgc      780 atcatctaaa taaaggtcag ctaataggtg aactttggtg agaccaaagg tgaactgcca      840
ggtcgaccaa attgctcgcc aagcagactc cgaaaaacac gggtaattca tatggcttgt      900
atctaatcca tactgaacag aggacctctc ctatgtctcg catttctgcg cgcactctgg      960
caatcgcact tgccggtgca accgcggcca gcctggcagt tgttccagca gcaacagcta     1020
atcctgccgg aaccgactcc agcacgcc                                        1048

<210> SEQ ID NO 4
<211> LENGTH: 1035
<212> TYPE: DNA
<213> ORGANISM: Corynebacterium glutamicum

<400> SEQUENCE: 4
taatcctgcc ggaaccgact ccagcacgcc tatggcatgg cttgtgcagg acggtggcga       60
gaccatcaag tccatccgca ccggcgacca ggtggaattc caggcaccag taatcttcga      120
ttaccgctac gacctgtgga aattccagcc aaccaccccct gtcaccggca acaccgcaag     180
ctccgacctt cctatcacct gggatgacac ccgcgcggct gagctagctt caatcaatga      240
cgttgctggc gaattccaca tcgcaagctt caacgtgctc aactacttca cctctctcgg      300
cgaagatgaa ccaggctgca gcgcatacag ggatatcaac aacaccccag tcaccgccaa      360
caactgtaac gtccgtggcg cttacaccga agaagcactc gaagatcagc agagcaagat      420
cgtcgaagca atcaaccgcc ttgacgtcga tgttcttgga cttgaagaaa tcgaaaacac      480
cgcgaccgtc accggcgacg tctcccgtcg cgatgacgca ctcaataccc tcgtcgcagc      540
actcaacgaa gcagttggat ccgatcgctg ggcggccgtc gaatctccag aacaattggg      600
caccgatgaa gactacatcc gcgtcgcctt catctacgac caaaccaccg tcaagcccgt      660
cggcgaatcc cgaatcttcg acgacgcagc cttcaccggc accgcacgcc agccactcgc      720
acaggaattc cagccactca acgacagcga gaaatccttc gtcggcgtag tcaaccactt      780
caagtccaag ggctctgtca ctcgtggaga cgccgacacc ggcgacggcc aaggcaacaa      840
cgccaacgtt cgcgtcgcac aggcacaggc actcatcgac cacctggaaa accaggacga      900
ctgggcatcc aagccaatct tcatcctcgg cgacaccaac tcctacgcca aggaaaccgc      960
gatgaccacc ctttacggcg ctggctacac caacatcgcc accgaattcg acgctctaga     1020
ttgacagcta gctca                                                      1035
```

```
<210> SEQ ID NO 5
<211> LENGTH: 110
<212> TYPE: DNA
<213> ORGANISM: Artificial Sequence
<220> FEATURE:
<223> OTHER INFORMATION: ExeR-1

<400> SEQUENCE: 5
acgctctaga ttgacagcta gctcagtcct aggtataatg gatccgaatt tctactgttg     60
tagatcctcg acggttggag cgttacattt aaataaaacg aaaggctcag                110

<210> SEQ ID NO 6
<211> LENGTH: 1186
<212> TYPE: DNA
<213> ORGANISM: Artificial Sequence
<220> FEATURE:
<223> OTHER INFORMATION: Amplified ATPase gene segment

<400> SEQUENCE: 6
gcctgcaggt cgactctaga ggatccatga ctgacattga tctggtggtg gaaaacgtcc     60
aaaggattat cgccaccaaa gagacaccgc cgacctctgc ggaaatagcg agcctgattc    120
gggaacaagc aggcgtgatc agtaacgagg acatcgtgat ggtgttgcgt cgactgcgca    180
gtgattctgt gggcgtggga ccgttggaat ctctgcttgc gcttcctggc gtgacggatg    240
tgttggttaa tgcccatgac agcgtgtgga ttgatcgcgg tcagggcgtg gagaaagtcg    300
acatggatct gggctcagag gaggcggtgc gtcgccttgc cacccggttg gcgttgacct    360
gtggcagacg cttagatgat gcgcagcctt tcgctgatgg ccgaatcacc agggacgacg    420
gcagcgtgtt gcgcattcac gcggtgttgg cacccttggc ggaatccggc acgtgcatca    480
gtgtgcgagt actgcgtcaa gcacggctga gccttgatga tcttatccaa agcggcacgg    540
tgcctgagga catcgcgcct gcgctccgga acatcatcaa tcaacggcgc tcgttccttg    600
ttgtcggtgg caccggcaca gggaaaacca cattgctgtc cgcgatgctc accgaagttc    660
ccgctgatca acgaatcatc tgcatcgagg acaccgcaga gcttcatccc ggccatccaa    720
gcaccatcaa cttggtgtct cgccaagcaa acgtcgaggg cgccggcgcc gtgagcatgg    780
cggatttgtt gaaacaatcg ctgcgcatga ggcctgaccg gattgtcgtc ggagagattc    840
gcggtgcgga agtcgtggat cttttggctg cgatgaatac cggacacgac ggcggtgctg    900
gcaccattca cgcgaactcc atctctgaag ttcccgcgcg catggaagct cttgcggcga   960
ccggcggatt ggaccgcatg gcattgcatt ctcaactcgc ggccgcagtg gacattgtgc   1020
tggtcatgaa acacacccct tttggccgca ggctagctca actcggggtg ctccgcggaa   1080
atcctgtgac cacgcaggtg gtgtgggatt tggaccacgg catgcacgaa gggagcgaag   1140
aggcatggtt tatgccctag ggatccccgg gtaccgagct cgaatt              1186

<210> SEQ ID NO 7
<211> LENGTH: 41
<212> TYPE: DNA
<213> ORGANISM: Artificial Sequence
<220> FEATURE:
<223> OTHER INFORMATION: Primer 1

<400> SEQUENCE: 7
aagtagaaca actgttcacc gggcccacgg aatcatctac c                         41
```

<210> SEQ ID NO 8
<211> LENGTH: 30
<212> TYPE: DNA
<213> ORGANISM: Artificial Sequence
<220> FEATURE:
<223> OTHER INFORMATION: Primer 2

<400> SEQUENCE: 8
ggcgtgctgg agtcggttcc ggcaggatta                              30

<210> SEQ ID NO 9
<211> LENGTH: 30
<212> TYPE: DNA
<213> ORGANISM: Artificial Sequence
<220> FEATURE:
<223> OTHER INFORMATION: Primer 3

<400> SEQUENCE: 9
taatcctgcc ggaaccgact ccagcacgcc                              30

<210> SEQ ID NO 10
<211> LENGTH: 35
<212> TYPE: DNA
<213> ORGANISM: Artificial Sequence
<220> FEATURE:
<223> OTHER INFORMATION: Primer 4

<400> SEQUENCE: 10
tgagctagct gtcaatctag agcgtcgaat tcggt                        35

<210> SEQ ID NO 11
<211> LENGTH: 25
<212> TYPE: DNA
<213> ORGANISM: Artificial Sequence
<220> FEATURE:
<223> OTHER INFORMATION: Primer 5

<400> SEQUENCE: 11
acgctctaga ttgacagcta gctca                                   25

<210> SEQ ID NO 12
<211> LENGTH: 60
<212> TYPE: DNA
<213> ORGANISM: Artificial Sequence
<220> FEATURE:
<223> OTHER INFORMATION: Primer 6

<400> SEQUENCE: 12
ctgagccttt cgttttattt aaatgtaacg ctccaaccgt cgaggatcta caacagtaga    60

<210> SEQ ID NO 13
<211> LENGTH: 46
<212> TYPE: DNA
<213> ORGANISM: Artificial Sequence
<220> FEATURE:
<223> OTHER INFORMATION: Primer 7

<400> SEQUENCE: 13
gcctgcaggt cgactctaga ggatccatga ctgacattga tctggt            46

<210> SEQ ID NO 14
<211> LENGTH: 46
<212> TYPE: DNA
<213> ORGANISM: Artificial Sequence
<220> FEATURE:
<223> OTHER INFORMATION: Primer 8

```
<400> SEQUENCE: 14
aattcgagct cggtacccgg ggatccctag ggcataaacc atgcct            46

<210> SEQ ID NO 15
<211> LENGTH: 20
<212> TYPE: DNA
<213> ORGANISM: Artificial Sequence
<220> FEATURE:
<223> OTHER INFORMATION: Primer 9

<400> SEQUENCE: 15
gtgagaccaa aggtgaactg                                         20

<210> SEQ ID NO 16
<211> LENGTH: 20
<212> TYPE: DNA
<213> ORGANISM: Artificial Sequence
<220> FEATURE:
<223> OTHER INFORMATION: Primer 10

<400> SEQUENCE: 16
gtaggttctg caggatcagt                                         20

<210> SEQ ID NO 17
<211> LENGTH: 20
<212> TYPE: DNA
<213> ORGANISM: Artificial Sequence
<220> FEATURE:
<223> OTHER INFORMATION: Primer 11

<400> SEQUENCE: 17
ggaattgtga gcggataaca                                         20

<210> SEQ ID NO 18
<211> LENGTH: 20
<212> TYPE: DNA
<213> ORGANISM: Artificial Sequence
<220> FEATURE:
<223> OTHER INFORMATION: Primer 12

<400> SEQUENCE: 18
gtatcaggct gaaaatcttc                                         20

<210> SEQ ID NO 19
<211> LENGTH: 1626
<212> TYPE: DNA
<213> ORGANISM: Artificial Sequence
<220> FEATURE:
<223> OTHER INFORMATION: Sequence after successful knockout of the ExeR
      gene

<400> SEQUENCE: 19
atgtctcgca tttctgcgcg cactctggca atcgcacttg ccggtgcaac cgcggccagc    60
ctggcagttg ttccagcagc aacagctaat cctgccggaa ccgactccag cacgcctatg   120
gcatggcttg tgcaggacgg tggcgagacc atcaagtcca tccgcaccgg cgaccaggtg   180
gaattccagg caccagtaat cttcgattac cgctacgacc tgtggaaatt ccagccaacc   240 accctgtca ccggcaacac cgcaagctcc gaccttccta tcacctggga tgacacccgc   300
gcggctgagc tagcttcaat caatgacgtt gctggcgaat ccacatcgc aagcttcaac   360 gtgctcaact acttcacctc tctcggcgaa gatgaaccag gctgcagcgc atacagggat   420
atcaacaaca ccccagtcac cgccaacaac tgtaacgtcc gtggcgctta caccgaagaa   480
```

-continued

```
gcactcgaag atcagcagag caagatcgtc gaagcaatca accgccttga cgtcgatgtt        540
cttggacttg aagaaatcga aaacaccgcg accgtcaccg cgacgtctc ccgtcgcgat         600 gacgcactca ataccctcgt cgcagcactc aacgaagcag ttggatccga tcgctgggcg        660
gccgtcgaat ctccagaaca attgggcacc gatgaagact acatccgcgt cgccttcatc       720
tacgaccaaa ccaccgtcaa gcccgtcggc gaatcccgaa tcttcgacga cgcagccttc       780
accggcaccg cacgccagcc actcgcacag gaattccagc cactcaacga cagcgagaaa       840
tccttcgtcg gcgtagtcaa ccacttcaag tccaagggct ctgtcactcg tggagacgcc       900
gacaccggcg acggccaagg caacaacgcc aacgttcgcg tcgcacaggc acaggcactc       960
atcgaccacc tggaaaacca ggacgactgg gcatccaagc caatcttcat cctcggcgac      1020
accaactcct acgccaagga aaccgcgatg accacccttt acggcgctgg ctacaccaac       1080
atcgccaccg aattcgacgc tggctacagc taccagttct ccggccgcat ggcagcctc       1140 gaccacgcac tcgcaacga agcagccatg aagcacgtca tcgacgccga ggtctgggac       1200
atcaacgctg acgaagcaat cgcattcgaa tactcccgtc gactcaacaa cacctccgac       1260
gtattcgaga caacgtcctt ccgctcctcc gaccacgacc cgatcaaggt cggattcaac       1320
ctcagcgaga ccactgagcc caccattccg gtagagccca ctgatcctgc agaacctacc       1380
gatccaacta ccccagttaa gccaactgat ccggtagaga ccacggatcc atctgagcca       1440
accgaccctg cagaacctac tgatccagct gaaccaactg accctgagga aacgaagaag       1500
ccagaggagc cgaagaaccc tggttcctcc aacggaagct cccaatacgc caccattgca       1560
gcaatcatcg cagcaatcct aggtgccatt gctttggcct ccagttcttc ccattcaag       1620 ttctaa                                                                  1626
```

<210> SEQ ID NO 20
<211> LENGTH: 11895
<212> TYPE: DNA
<213> ORGANISM: Artificial Sequence
<220> FEATURE:
<223> OTHER INFORMATION: Knockout plasmid (pJYS3_ExeR)

<400> SEQUENCE: 20

```
taattatcat tgactagccc atctcaattg gtatagtgat taaaatcacc tagaccaatt        60
gagatgtatg tctgaattag ttgttttcaa agcaaatgaa ctagcgatta gtcgctatga       120
cttaacggag catgaaacca agctaatttt atgctgtgtg gcactactca accccacgat       180
tgaaaaccct acaaggaaag aacggacggt atcgttcact tataaccaat acgctcagat       240
gatgaacatc agtagggaaa atgcttatgg tgtattagct aaagcaacca gagagctgat       300
gacgagaact gtggaaatca ggaatccttt ggttaaaggc tttgagattt ccagtggac       360 aaactatgcc aagttctcaa gcgaaaaatt agaattagtt tttagtgaag agatattgcc       420 ttatctttc cagttaaaaa aattcataaa atataatctg gaacatgtta agtcttttga       480
aaacaaatac tctatgagga tttatgagtg gttattaaaa gaactaacac aaaagaaaac       540
tcacaaggca aatatagaga ttagccttga tgaatttaag ttcatgttaa tgcttgaaaa       600
taactaccat gagtttaaaa ggcttaacca atgggttttg aaaccaataa gtaaagattt       660
aaacacttac agcaatatga aattggtggt tgataagcga ggccgcccga ctgatacgtt       720
gattttccaa gttgaactag atagacaaat ggatctcgta accgaacttg agaacaacca       780
gataaaaatg aatggtgaca aaataccaac aaccattaca tcagattcct acctacataa       840
cggactaaga aaaacactac acgatgcttt aactgcaaaa attcagctca ccagttttga       900
```

```
ggcaaaattt ttgagtgaca tgcaaagtaa gcatgatctc aatggttcgt tctcatggct      960
cacgcaaaaa caacgaacca cactagagaa catactggct aaatacgaaa ggatctgagg     1020
ttcttatggc tcttgtatct atcagtgaag catcaagact aacaaacaaa agtagaacaa     1080
ctgttcaccg ggcccacgga atcatctacc tcaagctcga agcgctttcc ctgacggaca     1140
tcggaaacgc cagaaactcc gatacgtccg agggcgcggt gtaccgcctg ccctgggga     1200 tccagaatct cagccttagg catgacattg acaactacac gggccacggt atttccctt     1260 actcaagaaa tggggaggac aatgttttac gagcacaagt gtaactgttg ccactggtca     1320
aacctagcca gcccttagat agggagattc tcctcgattg cttccactac ctcagctgca     1380
gatggttccg tccgaggagc aaagcgctta atcgtattac cttctgcatc taccaggaat     1440
ttctcaaaat tccactcgat ttcgctacca tcagttgcct cttttgagcac cttgtacagg     1500 gggtgggcac cctccccatt cacctcggtt ttgctcaaga gcgggaaggt gacgtcgtac     1560
tgattttgcg cgaaagcaca cacctcagcc tcggttccag gttcctggcc gttgaattga     1620
ttgcagggca cgccaatgac aaagaagcct cgatcttggt attcctcata cagtttttga     1680
agcccttcat actgtggcgt gagtccgcac ttggatgcca cgttcacgat gagcaaaagg     1740
tggcccgccc aatccgccat ggtggttct gtgccgtcgt tgagagttac gctgatgtca     1800
tgaatagaag tcataatcgc aaccctagtt gaggggagg atttagtgca tcatctaaat     1860
aaaggtcagc taataggtga actttggtga gaccaaggt gaactgccag gtcgaccaaa     1920
ttgctcgcca agcagactcc gaaaaacacg ggtaattcat atggcttgta tctaatccat     1980
actgaacaga ggacctctcc tatgtctcgc atttctgcgc gcactctggc aatcgcactt     2040
gccggtgcaa ccgcggccag cctggcagtt gttccagcag caacagctaa tcctgccgga     2100
accgactcca gcacgccat ggcatggctt gtgcaggacg gtggcgagac catcaagtcc     2160
atccgcaccg gcgaccaggt ggaattccag gcaccagtaa tcttcgatta ccgctacgac     2220
ctgtggaaat tccagccaac caccctgtc accggcaaca ccgcaagctc cgaccttcct     2280
atcacctggg atgacacccg cgcggctgag ctagcttcaa tcaatgacgt tgctggcgaa     2340
ttccacatcg caagcttcaa cgtgctcaac tacttcacct ctctcggcga agatgaacca     2400
ggctgcagcg catacaggga tatcaacaac accccagtca ccgccaacaa ctgtaacgtc     2460
cgtggcgctt acaccgaaga agcactcgaa gatcagcaga gcaagatcgt cgaagcaatc     2520
aaccgccttg acgtcgatgt tcttggactt gaagaaatcg aaaacaccgc gaccgtcacc     2580
ggcgacgtct cccgtcgcga tgacgcactc aatacctcg tcgcagcact caacgaagca     2640
gttggatccg atcgctgggc ggccgtcgaa tctccagaac aattgggcac cgatgaagac     2700
tacatccgcg tcgccttcat ctacgaccaa accaccgtca gcccgtcgg cgaatcccga     2760 atcttcgacg acgcagcctt caccggcacc gcacgccagc cactcgcaca ggaattccag     2820
ccactcaacg acagcgagaa atccttcgtc ggcgtagtca accacttcaa gtccaagggc     2880
tctgtcactc gtggagacgc cgacaccggc gacggcaag gcaacaacgc caacgttcgc     2940
gtcgcacagg cacaggcact catcgaccac ctggaaaacc aggacgactg ggcatccaag     3000
ccaatcttca tcctcggcga caccaactcc tacgccaagg aaaccgcgat gaccaccctt     3060
tacggcgctg gctacaccaa catcgccacc gaattcgacg ctctagattg acagctagct     3120
cagtcctagg tataatggat ccgaatttct actgttgtag atcctcgacg ttggagcgt     3180 tacatttaaa taaaacgaaa ggctcagtcg aaagactggg cctttcgttt tatctgttgt     3240
ttgtcggtga acgctctcct gagtaggaca aatccgccgg gagcggattt gaacgttgcg     3300
```

```
aagcaacggc ccggagggtg gcgggcagga cgcccgccat aaactgccag gcatcaaatt    3360
aagcagaagg ccatcctgac ggatggcctt tttgcgtttc tacaaactct taagcttgca    3420
tgcctgcagg tcgacttagt tattgcggtt ctggacaaat tcaaagtatt cttcgttctt    3480
aatgacgaga ttcagcttct tgccttcctg gttgttcttg atgcgaccca ggagcatgag    3540
acccttcaga ccgatgtggt aggcgccgtt tgcatcagcg tcctgtggca tgttctttgg    3600
agcctggcgg gaatcgaaga agttgccgtt gacgtcggcc actggggaga tgaggtaatc    3660
cagctcggtg ccggtcttgg agttgcgcat ctgcaggatg tgttgagca cagaggtcag     3720
cttttgcgaag aacttcttgt cggattcgcc gcagattgca gccttgatgc actcgccgtg   3780
gccgtattcg atggagtaat ccttcaggag cttctccagt tccttggttg ggtacacttc    3840
gcgggtatcc cagttgtggt tcttgtcgga gttgcgaaag ttgatgaggc gggagccgaa    3900
ggatgcgatg gtccacttgc ccttggctgc cttatcgccg aagttcttgt agtcgaagga    3960
gaattcgaag tagcccttat ccaggttgta gcagatcttg tcgaacttgg agaagaactc    4020
ctgggacttg gagacggatt cgtacttgg gtagagctgg ttgacgaagc cggtcactgg     4080
gcagatctta gaggtgaagc cagctggcac gtagtagatg atgccggtct gcttgcccat    4140
cttcttgaag gtctcgaatg gggcggtcag ctggtatgca cggaggacgc cgccggtctt    4200
atcgaattcg ttgtccttga acacgaggta gttcagcttc tcgatgagca tcttttccag    4260
cttctggtag acctgcttct ccaccttgaa gcggccgcgc ttgaagccga agttcaggtc    4320
ttcgaagacc acgattgcgt tgtactcgat caccagctta gcgatttcgt ggaccacctg    4380
ggagaggtag ccttccttca tttccttgat gttgttgatc ttcttccaat ccttgcgagc    4440
ggaatcgcgg tccttctcga tagcggccag cttgtcgtgg tagttggtct tcatgcgatc    4500
gttgccgatg atgttgaagg tgtcctgctt gatgatgttg cccttgccgt cgaccagggt    4560
gtagtaggcg aggtggcgtt cgccgcgatc gatggacagg atgtgcacgt cgttagcctt    4620
ctccttcagg agcaggttga tttcatcgtt gaacttgttg gcgccggagg acttgaagtt    4680
gatggtgatt gggcagtgga agaagaactt gtcctcggtg aagcgcttat ccttgatcag    4740
gtcgtactcg aacacggatt ccttctttgg gttatccttg ttcttgttgg cgattgcttc    4800
cttggctggg tgggtgatct tcttttggat ggactgcttg cggtagaaca gctctgcttc    4860
gccgttgagc ttgtagacca catcctgcag gttgcgttcg tcgaagagtg ccttccagta    4920
gagggtgtgc aggtttgggc ggcccttgga gtaagcggag aagtccttgt tgtagatctg    4980
gaagaggtac agcttgccct ggttgaccac ggaatcgatg taggactcgg agatgttttc    5040
gaaggtcagc ttgtagccct ggttctccac ttcgcggtag aattcatcga tggagttgta    5100
gcgctgggta tcgagaagc ggaagccgaa gtccttccac tctgggtgct ggagatgga     5160
ctgcttgtag aaatcgatga acttgcggca gtcttcgatg ttgaactcga acttttcgta    5220
gcccttctgt ggggagccgt tcttggtgtg ggtggagtgg ttgcggatgc gcaggatatc    5280
ttcggatggg ttgtagaact tgatggactt tgcgagaag aagacctttg ggagcatctt     5340
gttagcgcct gggagcagct tgtacacgat cttcttgtag ccctcgccct tgttttcctt    5400
gatgccttta tcgtcaagaga tcttgttgtt cttcttgttc atcacgccca ggtagtactt   5460
atcgtccttg atgaagagga tggcggtgtt atctggttcc ttgttcttgt cccagccgtt    5520
tgccagggtg gagttctcga agttgagctt gaacttttca tcggagtatg gcttctgggt    5580
gatgtagttc cggatcttgt tgtacagtgg gacgatgtta gcgagttcga agtagcactc    5640
ttcgaacacc aggtagaagt gctcatcctt gtcgaggatg ttggccttgt cttcggactg    5700
```

-continued

```
ggagatgtgg aagatcttca gcttgtggag caggttgttg gtctgatcga gcaggtcctt    5760
gattgccttc acatcgtcct cagcggaggc ctggagcaga tccttcttgc cctggttctg    5820
gtacttgatg gagatctggg ccaggttatc cttgttctgt gcgatttcgt cgaagatcat    5880
tgggattgca gcgaagtttg cgaggatctc ttcgaagcgg cactgcttat cgatgtcgcg    5940
gtgcttgttg aactcttcga gagccagctt gatggtctcg agggacaggt acttagcctt    6000
ttcggtcttc ttggcgatca gctcctgttc cttcttggat gggttatcga ggttctttgg    6060
ggcgatctgc tgggtgatgt attccaggac tgcggtgccg atcacggagt aatcgtcgaa    6120
gacctgctgg gagagatcgg tcagggactt gtcgttcttg aagtagatct tggagagatc    6180
cagcttctga gccttcagat cgtcgaagag cagggagagg gtctccttga tggacttctc    6240
ttccacggtc ttgaaggctg cgatctgttc gtagaaggac tgcatggtgg tgaccacatc    6300
ggaatcgtcc tccagcttgt cgatgacgaa ggacttggat tcggtgtcgg acaggatctg    6360
cttgaagagc acggacatct tgtacttctt cagggtctta tcgttgatct gctgggagta    6420
gaggttgatg tactcgttga tgcccttgcg cttggtgttt tcgccgttga cgaacttgcc    6480
gccgatgatg tgtgttgaact tggtgatgcc ggactggttc aggtagttgt tgaagttggc    6540
gatctcgaac acttcatcga gggagaagac gcgctggttc acttcagagg tcttgtaatc    6600
gatgtcgaag gtgagctctt cggccaggtc cttcttgatc tgctcgtagt tgatagcttc    6660
tggggcctta tccttcaggg actcgtactt tgccttgttt tcgaggaact ttggcaggtt    6720
atcgtcgacg atgcggtaga tgatagaggt tgggatatcg ttggaggagt acacgttctt    6780
gcggttttcg tggaagccct tgaagtaggt ggtccagccc ttgaaggact tgatgatctc    6840
cagagcttca tcgatgtcgg tgatgtcgga gttggccttg aagagctcga tgccgttatc    6900
cttggactgc ttgagccaca ggatgagatc ggattcctgg cccttctttg cgtcgatcag    6960
gttctggttg aagaggttct tgaacttctc ggaatccttg atgtattcgg agatctgctt    7020
cttgatggta tccttagcgg acttgaagtc cttctgcagg ttatcgtcat cggacttctt    7080
gagcttgaag tagacatcgg agtagttctg gagcaggtcc tcggagatgc acacggagga    7140
caggatctct tcgatgaaga actggtggta cttgtcgatg atctgctttg ccttcttgta    7200
atccttagcg cgcttttcgt catccaggat gaggccgcgt gccttgatgt tttcgagggt    7260
cttgccttgg gggatcagct caaaacggag ggtcttggac agggagtatt tattcacaaa    7320
ctcttggtag atggacatcg ttcaagtcct ttccaattcc acacatggta ccacacgatg    7380
attaattgta aacagctcag gtcatgattc cgcgaacccc agagtcccgc tcagaagaac    7440
tcgtcaagaa ggcgatagaa ggcgatgcgc tgcgaatcgg gagcggcgat accgtaaagc    7500
acgaggaagc ggtcagccca ttcgccgcca agctcttcag caatatcacg ggtagccaac    7560
gctatgtcct gatagcggtc cgccacaccc agccggccac agtcgatgaa tccagaaaag    7620
cggccatttt ccaccatgat attcggcaag caggcatcgc catgggtcac gacgagatcc    7680
tcgccgtcgg catccgcgc cttgagcctg gcgaacagtt cggctggcgc gagcccctga    7740
tgctcttcgt ccagatcatc ctgatcgaca agaccggctt ccatccgagt acgtgctcgc    7800
tcgatgcgat gtttcgcttg gtggtcgaat gggcaggtag ccggatcaag cgtatgcagc    7860
cgccgcattg catcagccat gatggatact ttctcggcag gagcaaggtg agatgacagg    7920
agatcctgcc ccggcacttc gcccaatagc agccagtccc ttcccgcttc agtgacaacg    7980
tcgagcacag ctgcgcaagg aacgcccgtc gtggccagcc acgatagccg cgctgcctcg    8040
tcttggagtt cattcagggc accggacagg tcggtcttga caaaaagaac cgggcgcccc    8100
```

-continued

```
tgcgctgaca gccggaacac ggcggcatca gagcagccga ttgtctgttg tgcccagtca      8160
tagccgaata gcctctccac ccaagcggcc ggagaacctg cgtgcaatcc atcttgttca      8220
atcatgcgaa acgatcctca tcctgtctct tgatcagatc ttgatcccct gcgccatcag      8280
atccttggcg gcaagaaagc catccagttt actttgcagg gcttcccaac cttaccagag      8340 ggcgcccag ctggcaattc cggttcgctt gctgtccata aaaccgccca gtctagctat       8400
cgccatgtaa gcccactgca agctacctgc tttctctttg cgcttgcgtt ttcccttgtc      8460
cagatagccc agtagctgac attcatccgg ggtcagcacc gtttctgcgg actggctttc      8520
tacgtgttcc gcttccggtg accgcctcga tgatcgccgg gtgggcgtgg cccaaggagg      8580
atcatccagc cattcggggt cgttcactgg ttccccttc tgatttctgg catagaagaa       8640
cccccgtgaa ctgtgtggtt ccggggttg ctgattttg cgagacttct cgcgcaattc        8700
cctagcttag gtgaaaacac catgaaacac tagggaaaca cccatgaaac acccattagg      8760
gcagtagggc ggcttcttcg tctagggctt gcatttgggc ggtgatctgg tctttagcgt      8820
gtgaaagtgt gtcgtaggtg gcgtgctcaa tgcactcgaa cgtcacgtca tttaccgggt      8880
cacggtgggc aaagagaact agtgggttag acattgtttt cctcgttgtc ggtggtggtg      8940
agcttttcta gccgctcggt aaacgcggcg atcatgaact cttggaggtt ttcaccgttc      9000
tgcatgcctg cgcgcttcat gtcctcacgt agtgccaaag gaacgcgtgc ggtgaccacg      9060
acgggcttag cctttgcctg cgcttctagt gcttcgatgg tggcttgtgc ctgcgcttgc      9120
tgcgcctgta gtgcctgttg agcttcttgt agttgctgtt ctagctgtgc cttggttgcc      9180
atgctttaag actctagtag cttccctgcg atatgtcatg cgcatgcgta gcaaacattg      9240
tcctgcaact cattcattat gtgcagtgct cctgttacta gtcgtacata ctcatattta      9300
cctagtctgc atgcagtgca tgcacatgca gtcatgtcgt gctaatgtgt aaaacatgta      9360
catgcagatt gctggggtg caggggcgg agccaccctg tccatgcggg gtgtggggct        9420
tgccccgccg gtacagacag tgagcaccgg ggcacctagt cgcggatacc cccctaggt       9480 atcggacacg taaccctccc atgtcgatgc aaatctttaa cattgagtac gggtaagctg      9540
gcacgcatag ccaagctagg cggccaccaa acaccactaa aaattaatag tcccctagaca     9600 agacaaaccc ccgtgcgagc taccaactca tatgcacggg ggccacataa cccgaagggg     9660
tttcaattga caaccatagc actagctaag acaacgggca caacacccgc acaaactcgc      9720
actgcgcaac cccgcacaac atcgggtcta ggtaacactg aaatagaagt gaacacctct      9780
aaggaaccgc aggtcaatga gggttctaag gtcactcgcg ctagggcgtg gcgtaggcaa      9840
aacgtcatgt acaagatcac caatagtaag gctctggcgg ggtgccatag gtggcgcagg     9900
gacgaagctg ttgcggtgtc ctggtcgtct aacggtgctt cgcagtttga gggtctgcaa      9960
aactctcact ctcgctgggg gtcatctctg gctgaattgg aagtcatggg cgaacgccgc     10020
attgagctgg ctattgctac taagaatcac ttggcggcgg gtggcgcgct catgatgttt     10080
gtgggcactg ttcgacacaa ccgctcacag tcatttgcgc aggttgaagc gggtattaag     10140
actgcgtact cttcgatggt gaaaacatct cagtggaaga agaacgtgc acggtacggg      10200 gtggagcaca cctatagtga ctatgaggtc acagactctt gggcgaacgg ttggcacttg     10260
caccgcaaca tgctgttgtt cttggatcgt ccactgtctg acgatgaact caaggcgttt     10320
gaggattcca tgttttcccg ctggtctgct ggtgtggtta aggccggtat ggacgcgcca     10380
ctgcgtgagc acgggtcaa acttgatcag gtgtctacct ggggtggaga cgctgcgaaa     10440
atggcaacct acctcgctaa gggcatgtct caggaactga ctggctccgc tactaaaacc     10500
```

```
gcgtctaagg ggtcgtacac gccgtttcag atgttggata tgttggccga tcaaagcgac    10560
gccggcgagg atatggacgc tgttttggtg gctcggtggc gtgagtatga ggttggttct    10620
aaaaacctgc gttcgtcctg gtcacgtggg gctaagcgtg ctttgggcat tgattacata    10680
gacgctgatg tacgtcgtga aatggaagaa gaactgtaca agctcgccgg tctggaagca    10740
ccggaacggg tcgaatcaac ccgcgttgct gttgctttgg tgaagcccga tgattggaaa    10800
ctgattcagt ctgatttcgc ggttaggcag tacgttctcg attgcgtgga taaggctaag    10860
gacgtggccg ctgcgcaacg tgtcgctaat gaggtgctgg caagtctggg tgtggattcc    10920
accccgtgca tgatcgttat ggatgatgtg gacttggacg cggttctgcc tactcatggg    10980
gacgctacta agcgtgatct gaatgcggcg gtgttcgcgg gtaatgagca gactattctt    11040
cgcacccact aaaagcggca taaaccccgt tcgatatttt gtgcgatgaa tttatggtca    11100
atgtcgcggg ggcaaactat gatgggtctt gttgttggcg tcccggagcg taaggatct    11160
aggtgaagat cctttttgat aatctcatga ccaaaatccc ttaacgtgag ttttcgttcc    11220
actgagcgtc agaccttgat gataccgctg ccttactggg tgcattagcc agtctgaatg    11280
acctgtcacg ggataatccg aagtggtcag actggaaaat cagagggcag gaactgctga    11340
acagcaaaaa gtcagatagc accacatagc agacccgcca taaaacgccc tgagaagccc    11400
gtgacgggct tttcttgtat tatgggtagt tccttgcat gaatccataa aaggcgcctg    11460
tagtgccatt tacccccatt cactgccaga gccgtgagcg cagcgaactg aatgtcacga    11520
aaaagacagc gactcaggtg cctgatggtc ggagacaaaa ggaatattca gcgatttgcc    11580
cgagcttgcg agggtgctac ttaagccttt agggttttaa ggtctgtttt gtagaggagc    11640
aaacagcgtt tgcgacatcc ttttgtaata ctgcggaact gactaaagta gtgagttata    11700
cacagggctg ggatctattc ttttttatctt tttttattct ttctttattc tataaattat    11760
aaccacttga atataaacaa aaaaaacaca caaggtcta gcggaattta cagagggtct    11820
agcagaattt acaagttttc cagcaaaggt ctagcagaat ttacagatac ccacaactca    11880
aaggaaaagg actag                                                      11895
```

<210> SEQ ID NO 21
<211> LENGTH: 7741
<212> TYPE: DNA
<213> ORGANISM: Artificial Sequence
<220> FEATURE:
<223> OTHER INFORMATION: Recombinant plasmid (pXMJ19*ATP)

<400> SEQUENCE: 21

```
aattaagctt gcatgcctgc aggtcgactc tagaggatcc atgactgaca ttgatctggt      60
ggtggaaaac gtccaaagga ttatcgccac caaagagaca ccgccgacct ctgcggaaat     120
agcgagcctg attcgggaac aagcaggcgt gatcagtaac gaggacatcg tgatggtgtt     180
gcgtcgactg cgcagtgatt ctgtgggcgt gggaccgttg aatctctgc ttgcgcttcc      240
tggcgtgacg gatgtgttgg ttaatgccca tgacagcgtg tggattgatc gcggtcaggg     300
cgtggagaaa gtcgacatgg atctgggctc agaggaggcg gtgcgtcgcc ttgccacccg     360
gttggcgttg acctgtggca gacgcttaga tgatgcgcag cctttcgctg atggccgaat     420
caccagggac gacggcagcg tgttgcgcat tcacgcggtg ttggcaccct ggcggaatc      480
cggcacgtgc atcagtgtgc gagtactgcg tcaagcacgg ctgagccttg atgatcttat     540
ccaaagcggc acggtgcctg aggacatcgc gcctgcgctc cggaacatca tcaatcaacg     600
gcgctcgttc cttgttgtcg gtggcaccgg cacagggaaa accacattgc tgtccgcgat     660
```

```
gctcaccgaa gttcccgctg atcaacgaat catctgcatc gaggacaccg cagagcttca    720
tcccggccat ccaagcacca tcaacttggt gtctcgccaa gcaaacgtcg agggcgccgg    780
cgccgtgagc atggcggatt tgttgaaaca atcgctgcgc atgaggcctg accggattgt    840
cgtcggagag attcgcggtg cggaagtcgt ggatcttttg gctgcgatga ataccggaca    900
cgacggcggt gctggcacca ttcacgcgaa ctccatctct gaagttcccg cgcgcatgga    960
agctcttgcg gcgaccggcg gattggaccg catggcattg cattctcaac tcgcggccgc   1020
agtggacatt gtgctggtca tgaaacacac ccctttggc cgcaggctag ctcaactcgg    1080
ggtgctccgc ggaaatcctg tgaccacgca gtggtgtgg gatttggacc acggcatgca    1140
cgaagggagc gaagaggcat ggtttatgcc ctagggatcc ccgggtaccg agctcgaatt   1200
cagcttggct gttttggcgg atgagagaag attttcagcc tgatacagat taaatcagaa   1260
cgcagaagcg gtctgataaa acagaatttg cctggcggca gtagcgcggt ggtcccacct   1320 gacccccatgc cgaactcaga gtgaaacgc cgtagcgccg atggtagtgt ggggtctccc   1380
catgcgagag tagggaactg ccaggcatca aataaaacga aaggctcagt cgaaagactg   1440
ggcctttcgt tttatctgtt gtttgtcggt gaacgctctc ctgagtagga caaatccgcc   1500
gggagcggat ttgaacgttg cgaagcaacg gcccggaggg tggcgggcag gacgcccgcc   1560
ataaactgcc aggcatcaaa ttaagcagaa ggccatcctg acggatggcc ttttttgcgtt   1620 tctacaaact cttttgttta tttttctaaa tacattcaaa tatgtatccg ctcatgagac   1680
aataaccctg ataaatgctt caataatatt gaaaaaggaa gagtatgagt attcaacatt   1740
tccgtgtcgc ccttattccc ttttttgcgg cattttgcct tcctgttttt gctcacccag   1800
aaacgctggt gaaagtaaaa gatgctgaag atcagttggg tgcacgagtg ggttacatcg   1860
aactggatct caacagcggt aagatccttg agagttttcg ccccgaagaa cgttttccaa   1920
tgatgagcac ttttgcttcc tcgctcactg actcgctgcg ctcggtcgtt cggctgcggc   1980
gagcggtatc agctcactca aaggcggtaa tacggttatc cacagaatca ggggataacg   2040
caggaaagaa catgtgagca aaaggccagc aaaaggccag gaaccgtaaa aaggccgcgt   2100
tgctggcgtt tttccatagg ctccgccccc ctgacgagca tcacaaaaat cgacgctcaa   2160
gtcagaggtg gcgaaacccg acaggactat aaagatacca ggcgtttccc cctggaagct   2220
ccctcgtgcg ctctcctgtt ccgaccctgc cgcttaccgg atacctgtcc gcctttctcc   2280
cttcgggaag cgtggcgctt tctcaatgct cacgctgtag gtatctcagt tcggtgtagg   2340
tcgttcgctc caagctgggc tgtgtgcacg aaccccccgt tcagcccgac cgctgcgcct   2400
tatccggtaa ctatcgtctt gagtccaacc cggtaagaca cgacttatcg ccactggcag   2460
cagccactgg taacaggatt agcagagcga ggtatgtagg cggtgctaca gagttcttga   2520
agtggtggcc taactacggc tacactagaa ggacagtatt tggtatctgc gctctgctga   2580
agccagttac cttcggaaaa agagttggta gctcttgatc cggcaaacaa accaccgctg   2640
gtagcggtgg tttttttgtt tgcaagcagc agattacgcg cagaaaaaaa ggatctcaag   2700
aagatccttt gatcttttct acggggtctg acgctcagtg gaacgaaaac tcacgttaag   2760
ggattttggt catgagatta tcaaaaagga tcttcaccta gatcctttg gggtgggcga   2820 agaactccag catgagatcc ccgcgctgga ggatcatcca gccattcggg tcgttcact    2880 ggttccccttt tctgatttct ggcatagaag aaccccgtg aactgtgtgg ttccgggggt    2940
tgctgatttt tgcgagactt ctcgcgcaat tccctagctt aggtgaaaac accatgaaac   3000
actagggaaa cacccatgaa acacccatta gggcagtagg gcggcttctt cgtctagggc   3060
```

```
ttgcatttgg gcggtgatct ggtctttagc gtgtgaaagt gtgtcgtagg tggcgtgctc    3120
aatgcactcg aacgtcacgt catttaccgg gtcacggtgg gcaaagagaa ctagtgggtt    3180
agacattgtt ttcctcgttg tcggtggtgg tgagcttttc tagccgctcg gtaaacgcgg    3240
cgatcatgaa ctcttggagg ttttcaccgt tctgcatgcc tgcgcgcttc atgtcctcac    3300
gtagtgccaa aggaacgcgt gcggtgacca cgacgggctt agcctttgcc tgcgcttcta    3360
gtgcttcgat ggtggcttgt gcctgcgctt gctgcgcctg tagtgcctgt tgagcttctt    3420
gtagttgctg ttctagctgt gccttggttg ccatgcttta agactctagt agctttcctg    3480
cgatatgtca tgcgcatgcg tagcaaacat tgtcctgcaa ctcattcatt atgtgcagtg    3540
ctcctgttac tagtcgtaca tactcatatt tacctagtct gcatgcagtg catgcacatg    3600
cagtcatgtc gtgctaatgt gtaaaacatg tacatgcaga ttgctggggg tgcagggggc    3660
ggagccaccc tgtccatgcg gggtgtgggg cttgccccgc cggtacagac agtgagcacc    3720
ggggcaccta gtcgcggata ccccccctag gtatcggaca cgtaaccctc ccatgtcgat    3780
gcaaatcttt aacattgagt acgggtaagc tggcacgcat agccaagcta ggcggccacc    3840
aaacaccact aaaaattaat agtccctaga caagacaaac cccgtgcga gctaccaact    3900 catatgcacg ggggccacat aacccgaagg ggtttcaatt gacaaccata gcactagcta    3960
agacaacggg cacaacaccc gcacaaactc gcactgcgca accccgcaca acatcgggtc    4020
taggtaacac tgagtaacac tgaaatagaa gtgaacacct ctaaggaacc gcaggtcaat    4080
gagggttcta aggtcactcg cgctagggcg tggcgtaggc aaaacgtcat gtacaagatc    4140
accaatagta aggctctggc ggggtgccat aggtggcgca gggacgaagc tgttgcggtg    4200
tcctggtcgt ctaacggtgc ttcgcagttt gagggtctgc aaaactctca ctctcgctgg    4260
gggtcacctc tggctgaatt ggaagtcatg gcgaacgcc gcattgagct ggctattgct    4320
actaagaatc acttggcggc gggtggcgcg ctcatgatgt ttgtgggcac tgttcgacac    4380
aaccgctcac agtcatttgc gcaggttgaa gcgggtatta agactgcgta ctcttcgatg    4440
gtgaaaacat ctcagtggaa gaaagaacgt gcacggtacg gggtggagca cacctatagt    4500
gactatgagg tcacagactc ttgggcgaac ggttggcact tgcaccgcaa catgctgttg    4560
ttcttggatc gtccactgtc tgacgatgaa ctcaaggcgt ttgaggattc catgttttcc    4620
cgctggtctg ctggtgtggt taaggccggt atggacgcgc cactgcgtga gcacggggtc    4680
aaacttgatc aggtgtctac ctggggtgga gacgctgcga aaatggcaac ctacctcgct    4740
aagggcatgt ctcaggaact gactggctcc gctactaaaa ccgcgtctaa ggggtcgtac    4800
acgccgtttc agatgttgga tatgttggcc gatcaaagcg acgccggcga ggatatggac    4860
gctgttttgg tggctcggtg gcgtgagtat gaggttggtt ctaaaaacct gcgttcgtcc    4920
tggtcacgtg gggctaagcg tgctttgggc attgattaca tagacgctga tgtacgtcgt    4980
gaaatggaag aagaactgta caagctcgcc ggtctggaag caccggaacg ggtcgaatca    5040
acccgcgttg ctgttgcttt ggtgaagccc gatgattgga aactgattca gtctgatttc    5100
gcggttaggc agtacgttct cgattgcgtg gataaggcta aggacgtggc cgctgcgcaa    5160
cgtgtcgcta atgaggtgct ggcaagtctg ggtgtggatt ccaccccgtg catgatcgtt    5220
atggatgatg tggacttgga cgcggttctg cctactcatg gggacgctac taagcgtgat    5280
ctgaatgcgg cggtgttcgc gggtaatgag cagactattc ttcgcaccca ctaaaagcgg    5340
cataaacccc gttcgatatt ttgtgcgatg aatttatggt caatgtcgcg ggggcaaact    5400
atgatgggtc ttgttgttgg cgtcccggaa aacgattccg aagcccaacc tttcatagaa    5460
```

-continued

| | |
|---|---|
| ggcggcggtg gaatcgaaat ctcgtgatgg caggttgggc gtcgcttggt cggtcatttc | 5520 |
| gaagggcacc aataactgcc ttaaaaaaat tacgccccgc cctgccactc atcgcagtac | 5580 |
| tgttgtaatt cattaagcat tctgccgaca tggaagccat cacagacggc atgatgaacc | 5640 |
| tgaatcgcca gcggcatcag caccttgtcg ccttgcgtat aatatttgcc catggtgaaa | 5700 |
| acgggggcga agaagttgtc catattggcc acgtttaaat caaaactggt gaaactcacc | 5760 |
| cagggattgg ctgagacgaa aaacatattc tcaataaacc ctttagggaa ataggccagg | 5820 |
| ttttcaccgt aacacgccac atcttgcgaa tatatgtgta gaaactgccg gaaatcgtcg | 5880 |
| tggtattcac tccagagcga tgaaaacgtt tcagtttgct catggaaaac ggtgtaacaa | 5940 |
| gggtgaacac tatcccatat caccagctca ccgtctttca ttgccatacg gaactccgga | 6000 |
| tgagcattca tcaggcgggc aagaatgtga ataaaggccg gataaaactt gtgcttattt | 6060 |
| ttctttacgg tctttaaaaa ggccgtaata tccagctgaa cggtctggtt ataggtacat | 6120 |
| tgagcaactg actgaaatgc ctcaaaatgt tctttacgat gccattggga tatatcaacg | 6180 |
| gtggtatatc cagtgatttt tttctccatt ttagcttcct tagctcctga aaatctcgtc | 6240 |
| gaagctcggc ggatttgtcc tactcaagct gatccgacaa aatccacaca ttatcccagg | 6300 |
| tgtccggatc ggtcaaatac gctgccagct catagaccgt atccaaagca tccgggctg | 6360 |
| atccccggcg ccagggtggt ttttcttttc accagtgaga cgggcaacag ctgattgccc | 6420 |
| ttcaccgcct ggccctgaga gagttgcagc aagcggtcca cgtggtttgc cccagcaggc | 6480 |
| gaaaatcctg tttgatggtg gttaacggcg ggatataaca tgagctgtct tcggtatcgt | 6540 |
| cgtatcccac taccgagata tccgcaccaa cgcgcagccc ggactcggta atggcgcgca | 6600 |
| ttgcgcccag cgccatctga tcgttggcaa ccagcatcgc agtgggaacg atgccctcat | 6660 |
| tcagcatttg catggtttgt tgaaaaccgg acatggcact ccagtcgcct tcccgttccg | 6720 |
| ctatcggctg aatttgattg cgagtgagat atttatgcca gccagccaga cgcagacgcg | 6780 |
| ccgagacaga acttaatggg cccgctaaca gcgcgatttg ctggtgaccc aatgcgacca | 6840 |
| gatgctccac gcccagtcgc gtaccgtctt catgggagaa aataatactg ttgatgggtg | 6900 |
| tctggtcaga gacatcaaga aataacgccg gaacattagt gcaggcagct tccacagcaa | 6960 |
| tggcatcctg gtcatccagc ggatagttaa tgatcagccc actgacgcgt tgcgcgagaa | 7020 |
| gattgtgcac cgccgcttta caggcttcga cgccgcttcg ttctaccatc gacaccacca | 7080 |
| cgctggcacc cagttgatcg gcgcgagatt taatcgccgc gacaatttgc gacggcgcgt | 7140 |
| gcagggccag actggaggtg gcaacgccaa tcagcaacga ctgtttgccc gccagttgtt | 7200 |
| gtgccacgcg gttgggaatg taattcagct ccgccatcgc cgcttccact ttttcccgcg | 7260 |
| ttttcgcaga aacgtggctg gcctggttca ccacgcggga aacggtctga taagagacac | 7320 |
| cggcatactc tgcgacatcg tataacgtta ctggtttcac attcaccacc ctgaattgac | 7380 |
| tctcttccgg gcgctatcat gccataccgc gaaaggtttt gcaccattcg atggtgtcaa | 7440 |
| cgtaaatgcc gcttcgcctt cgcgcgcgaa ttgcaagctg atccgggctt atcgactgca | 7500 |
| cggtgcacca atgcttctgg cgtcaggcag ccatcggaag ctgtggtatg gctgtgcagg | 7560 |
| tcgtaaatca ctgcataatt cgtgtcgctc aaggcgcact cccgttctgg ataatgtttt | 7620 |
| ttgcgccgac atcataacgg ttctggcaaa tattctgaaa tgagctgttg acaattaatc | 7680 |
| atcggctcgt ataatgtgtg gaattgtgag cggataacaa tttcacacag gaaacagaat | 7740 |
| t | 7741 |

<210> SEQ ID NO 22
<211> LENGTH: 21
<212> TYPE: DNA
<213> ORGANISM: Artificial Sequence
<220> FEATURE:
<223> OTHER INFORMATION: Recognition sequence on ExeR gene

<400> SEQUENCE: 22
cctcgacggt tggagcgtta c                                              21

<210> SEQ ID NO 23
<211> LENGTH: 21
<212> TYPE: DNA
<213> ORGANISM: Artificial Sequence
<220> FEATURE:
<223> OTHER INFORMATION: Recognition sequence on crtYf gene

<400> SEQUENCE: 23
caggcaacca tagggcagga a                                              21

<210> SEQ ID NO 24
<211> LENGTH: 6601
<212> TYPE: DNA
<213> ORGANISM: Artificial Sequence
<220> FEATURE:
<223> OTHER INFORMATION: plasmid (pXMJ19)

<400> SEQUENCE: 24
aattaagctt gcatgcctgc aggtcgactc tagaggatcc ccgggtaccg agctcgaatt      60
cagcttggct gttttggcgg atgagagaag attttcagcc tgatacagat taaatcagaa     120
cgcagaagcg gtctgataaa acagaatttg cctggcggca gtagcgcggt ggtcccacct     180
gaccccatgc cgaactcaga agtgaaacgc cgtagcgccg atggtagtgt ggggtctccc     240
catgcgagag tagggaactg ccaggcatca aataaaacga aaggctcagt cgaaagactg     300
ggcctttcgt tttatctgtt gtttgtcggt gaacgctctc ctgagtagga caaatccgcc     360
gggagcggat ttgaacgttg cgaagcaacg gcccggaggg tggcgggcag gacgcccgcc     420
ataaactgcc aggcatcaaa ttaagcagaa ggccatcctg acggatggcc ttttttgcgtt     480 tctacaaact cttttgttta ttttttctaaa tacattcaaa tatgtatccg ctcatgagac     540
aataaccctg ataaatgctt caataatatt gaaaaaggaa gagtatgagt attcaacatt     600
tccgtgtcgc ccttattccc ttttttgcgg cattttgcct tcctgttttt gctcacccag     660
aaacgctggt gaaagtaaaa gatgctgaag atcagttggg tgcacgagtg gttacatcg     720 aactggatct caacagcggt aagatccttg agagttttcg ccccgaagaa cgttttccaa     780
tgatgagcac ttttgcttcc tcgctcactg actcgctgcg ctcggtcgtt cggctgcggc     840
gagcggtatc agctcactca aaggcggtaa tacggttatc cacagaatca ggggataacg     900
caggaaagaa catgtgagca aaaggccagc aaaaggccag gaaccgtaaa aaggccgcgt     960
tgctggcgtt tttccatagg ctccgccccc ctgacgagca tcacaaaaat cgacgctcaa    1020
gtcagaggtg gcgaaacccg acaggactat aaagatacca ggcgtttccc cctggaagct    1080
ccctcgtgcg ctctcctgtt ccgaccctgc cgcttaccgg atacctgtcc gcctttctcc    1140
cttcgggaag cgtggcgctt tctcaatgct cacgctgtag gtatctcagt tcggtgtagg    1200
tcgttcgctc caagctgggc tgtgtgcacg aaccccccgt tcagcccgac cgctgcgcct    1260
tatccggtaa ctatcgtctt gagtccaacc cggtaagaca cgacttatcg ccactggcag    1320
cagccactgg taacaggatt agcagagcga ggtatgtagg cggtgctaca gagttcttga    1380

```
agtggtggcc taactacggc tacactagaa ggacagtatt tggtatctgc gctctgctga    1440
agccagttac cttcggaaaa agagttggta gctcttgatc cggcaaacaa accaccgctg    1500
gtagcggtgg ttttttttgtt tgcaagcagc agattacgcg cagaaaaaaa ggatctcaag    1560
aagatccttt gatcttttct acggggtctg acgctcagtg gaacgaaaac tcacgttaag    1620
ggattttggt catgagatta tcaaaaagga tcttcaccta gatccttttg gggtgggcga    1680
agaactccag catgagatcc ccgcgctgga ggatcatcca gccattcggg gtcgttcact    1740
ggttcccctt tctgatttct ggcatagaag aaccccgtg aactgtgtgg ttccgggggt    1800
tgctgatttt tgcgagactt ctcgcgcaat tccctagctt aggtgaaaac accatgaaac    1860
actagggaaa cacccatgaa acacccatta gggcagtagg gcggcttctt cgtctagggc    1920
ttgcatttgg gcggtgatct ggtctttagc gtgtgaaagt gtgtcgtagg tggcgtgctc    1980
aatgcactcg aacgtcacgt catttaccgg gtcacggtgg gcaaagagaa ctagtgggtt    2040
agacattgtt ttcctcgttg tcggtggtgg tgagcttttc tagccgctcg gtaaacgcgg    2100
cgatcatgaa ctcttggagg ttttcaccgt tctgcatgcc tgcgcgcttc atgtcctcac    2160
gtagtgccaa aggaacgcgt gcggtgacca cgacgggctt agcctttgcc tgcgcttcta    2220
gtgcttcgat ggtggcttgt gcctgcgctt gctgcgcctg tagtgcctgt tgagcttctt    2280
gtagttgctg ttctagctgt gccttggttg ccatgcttta agactctagt agctttcctg    2340
cgatatgtca tgcgcatgcg tagcaaacat tgtcctgcaa ctcattcatt atgtgcagtg    2400
ctcctgttac tagtcgtaca tactcatatt tacctagtct gcatgcagtg catgcacatg    2460
cagtcatgtc gtgctaatgt gtaaaacatg tacatgcaga ttgctggggg tgcagggggc    2520
ggagccaccc tgtccatgcg gggtgtgggg cttgccccgc cggtacagac agtgagcacc    2580
ggggcaccta gtcgcggata cccccccctag gtatcggaca cgtaaccctc ccatgtcgat    2640
gcaaatcttt aacattgagt acgggtaagc tggcacgcat agccaagcta ggcggccacc    2700
aaacaccact aaaaattaat agtccctaga caagacaaac cccgtgcga gctaccaact    2760
catatgcacg ggggccacat aacccgaagg ggtttcaatt gacaaccata gcactagcta    2820
agacaacggg cacaacaccc gcacaaactc gcactgcgca accccgcaca acatcgggtc    2880
taggtaacac tgagtaacac tgaaatagaa gtgaacacct ctaaggaacc gcaggtcaat    2940
gagggttcta aggtcactcg cgctagggcg tggcgtaggc aaaacgtcat gtacaagatc    3000
accaatagta aggctctggc ggggtgccat aggtggcgca gggacgaagc tgttgcggtg    3060
tcctggtcgt ctaacggtgc ttcgcagttt gagggtctgc aaaactctca ctctcgctgg    3120
gggtcacctc tggctgaatt ggaagtcatg ggcgaacgcc gcattgagct ggctattgct    3180
actaagaatc acttggcggc gggtggcgcg ctcatgatgt ttgtgggcac tgttcgacac    3240
aaccgctcac agtcatttgc gcaggttgaa gcgggtatta agactgcgta ctcttcgatg    3300
gtgaaaacat ctcagtggaa gaagaacgt gcacggtacg gggtggagca cacctatagt    3360
gactatgagg tcacagactc ttgggcgaac ggttggcact gcaccgcaa catgctgttg    3420
ttcttggatc gtccactgtc tgacgatgaa ctcaaggcgt ttgaggattc catgtttttcc    3480
cgctggtctg ctggtgtggt taaggccggt atggacgcgc cactgcgtga gcacggggtc    3540
aaacttgatc aggtgtctac ctgggggtgga gacgctgcga aaatggcaac ctacctcgct    3600
aagggcatgt ctcaggaact gactggctcc gctactaaaa ccgcgtctaa ggggtcgtac    3660
acgccgtttc agatgttgga tatgttggcc gatcaaagcg acgccggcga ggatatggac    3720
gctgtttttgg tggctcggtg gcgtgagtat gaggttggtt ctaaaaacct gcgttcgtcc    3780
```

-continued

```
tggtcacgtg gggctaagcg tgctttgggc attgattaca tagacgctga tgtacgtcgt    3840
gaaatggaag aagaactgta caagctcgcc ggtctggaag caccggaacg ggtcgaatca    3900
acccgcgttg ctgttgcttt ggtgaagccc gatgattgga aactgattca gtctgatttc    3960
gcggttaggc agtacgttct cgattgcgtg gataaggcta aggacgtggc cgctgcgcaa    4020
cgtgtcgcta atgaggtgct ggcaagtctg ggtgtggatt ccaccccgtg catgatcgtt    4080
atggatgatg tggacttgga cgcggttctg cctactcatg gggacgctac taagcgtgat    4140
ctgaatgcgg cggtgttcgc gggtaatgag cagactattc ttcgcaccca ctaaaagcgg    4200
cataaacccc gttcgatatt ttgtgcgatg aatttatggt caatgtcgcg ggggcaaact    4260
atgatgggtc ttgttgttgg cgtcccggaa aacgattccg aagcccaacc tttcatagaa    4320
ggcggcggtg gaatcgaaat ctcgtgatgg caggttgggc gtcgcttggt cggtcatttc    4380
gaagggcacc aataactgcc ttaaaaaaat tacgccccgc cctgccactc atcgcagtac    4440
tgttgtaatt cattaagcat tctgccgaca tggaagccat cacagacggc atgatgaacc    4500
tgaatcgcca gcggcatcag caccttgtcg ccttgcgtat aatatttgcc catggtgaaa    4560 acggggggcga agaagttgtc catattggcc acgtttaaat caaaactggt gaaactcacc    4620
cagggattgg ctgagacgaa aaacatattc tcaataaacc ctttagggaa ataggccagg    4680
ttttcaccgt aacacgccac atcttgcgaa tatatgtgta gaaactgccg gaaatcgtcg    4740
tggtattcac tccagagcga tgaaaacgtt tcagtttgct catggaaaac ggtgtaacaa    4800
gggtgaacac tatcccatat caccagctca ccgtctttca ttgccatacg gaactccgga    4860
tgagcattca tcaggcgggc aagaatgtga ataaaggccg gataaaactt gtgcttattt    4920
ttctttacgg tctttaaaaa ggccgtaata tccagctgaa cggtctggtt ataggtacat    4980
tgagcaactg actgaaatgc ctcaaaatgt tctttacgat gccattggga tatatcaacg    5040
gtggtatatc cagtgatttt tttctccatt ttagcttcct tagctcctga aaatctcgtc    5100
gaagctcggc ggatttgtcc tactcaagct gatccgacaa aatccacaca ttatcccagg    5160
tgtccggatc ggtcaaatac gctgccagct catagaccgt atccaaagca tccggggctg    5220
atccccggcg ccaggtggt ttttcttttc accagtgaga cgggcaacag ctgattgccc    5280
ttcaccgcct ggccctgaga gagttgcagc aagcggtcca cgtggtttgc cccagcaggc    5340
gaaaatcctg tttgatggtg gttaacggcg ggatataaca tgagctgtct tcggtatcgt    5400
cgtatcccac taccgagata tccgcaccaa cgcgcagccc ggactcggta atggcgcgca    5460
ttgcgcccag cgccatctga tcgttggcaa ccagcatcgc agtgggaacg atgccctcat    5520
tcagcatttg catggtttgt tgaaaaccgg acatggcact ccagtcgcct tcccgttccg    5580
ctatcggctg aatttgattg cgagtgagat atttatgcca gccagccaga cgcagacgcg    5640
ccgagacaga acttaatggg cccgctaaca gcgcgatttg ctggtgaccc aatgcgacca    5700
gatgctccac gcccagtcgc gtaccgtctt catgggagaa aataatactg ttgatgggtg    5760
tctggtcaga gacatcaaga aataacgccg gaacattagt gcaggcagct ccacagcaa    5820 tggcatcctg gtcatccagc ggatagttaa tgatcagccc actgacgcgt tgcgcgagaa    5880
gattgtgcac cgccgcttta caggcttcga cgccgcttcg ttctaccatc gacaccacca    5940
cgctggcacc cagttgatcg gcgcgagatt taatcgccgc gacaatttgc gacggcgcgt    6000
gcagggccag actggaggtg gcaacgccaa tcagcaacga ctgtttgccc gccagttgtt    6060
gtgccacgcg gttgggaatg taattcagct ccgccatcgc cgcttccact ttttcccgcg    6120
ttttcgcaga acgtggctg gcctggttca ccacgcggga aacggtctga taagagacac    6180
```

```
cggcatactc tgcgacatcg tataacgtta ctggtttcac attcaccacc ctgaattgac    6240
tctcttccgg gcgctatcat gccataccgc gaaaggtttt gcaccattcg atggtgtcaa    6300
cgtaaatgcc gcttcgcctt cgcgcgcgaa ttgcaagctg atccgggctt atcgactgca    6360
cggtgcacca atgcttctgg cgtcaggcag ccatcggaag ctgtggtatg gctgtgcagg    6420
tcgtaaatca ctgcataatt cgtgtcgctc aaggcgcact cccgttctgg ataatgtttt    6480
ttgcgccgac atcataacgg ttctggcaaa tattctgaaa tgagctgttg acaattaatc    6540
atcggctcgt ataatgtgtg gaattgtgag cggataacaa tttcacacag gaaacagaat    6600
t                                                                    6601

<210> SEQ ID NO 25
<211> LENGTH: 1494
<212> TYPE: DNA
<213> ORGANISM: Artificial Sequence
<220> FEATURE:
<223> OTHER INFORMATION: Knocked out ExeR gene PCR (DNA)

<400> SEQUENCE: 25
gtgagaccaa aggtgaactg ccaggtcgac caaattgctc gccaagcaga ctccgaaaaa      60
cacgggtaat tcatatggct tgtatctaat ccatactgaa cagaggacct ctcctatgtc     120
tcgcatttct gcgcgcactc tggcaatcgc acttgccggt gcaaccgcgg ccagcctggc     180
agttgttcca gcagcaacag ctaatcctgc cggaaccgac tccagcacgc ctatggcatg     240
gcttgtgcag gacggtggcg agaccatcaa gtccatccgc accggcgacc aggtggaatt     300
ccaggcacca gtaatcttcg attaccgcta cgacctgtgg aaattccagc caaccacccc     360
tgtcaccggc aacaccgcaa gctccgacct tcctatcacc tgggatgaca cccgcgcggc     420
tgagctagct tcaatcaatg acgttgctgg cgaattccac atcgcaagct caacgtgct     480 caactacttc acctctctcg gcgaagatga accaggctgc agcgcataca gggatatcaa     540
caacacccca gtcaccgcca acaactgtaa cgtccgtggc gcttacaccg aagaagcact     600
cgaagatcag cagagcaaga tcgtcgaagc aatcaaccgc cttgacgtcg atgttcttgg     660
acttgaagaa atcgaaaaca ccgcgaccgt caccggcgac gtctcccgtc gcgatgacgc     720
actcaatacc ctcgtcgcag cactcaacga agcagttgga tccgatcgct gggcggccgt     780
cgaatctcca gaacaattgg gcaccgatga agactacatc cgcgtcgcct tcatctacga     840
ccaaaccacc gtcaagcccg tcggcgaatc ccgaatcttc gacgacgcag ccttcaccgg     900
caccgcacgc cagccactcg cacaggaatt ccagccactc aacgacagcg agaaatcctt     960
cgtcggcgta gtcaaccact tcaagtccaa gggctctgtc actcgtggag acgccgacac    1020
cggcgacggc caaggcaaca acgccaacgt tcgcgtcgca caggcacagg cactcatcga    1080
ccacctggaa aaccaggacg actgggcatc caagccaatc ttcatcctcg gcgacaccaa    1140
ctcctacgcc aaggaaaccg cgatgaccac cctttacggc gctggctaca ccaacatcgc    1200
caccgaattc gacgctggct acagctacca gttctccggc gcattggca gcctcgacca    1260 cgcactcggc aacgaagcag ccatgaagca cgtcatcgac gccgaggtct gggacatcaa    1320
cgctgacgaa gcaatcgcat tcgaatactc ccgtcgactc aacaacacct ccgacgtatt    1380
cgagaacaac gtcttccgct cctccgacca cgacccgatc aaggtcggat tcaacctcag    1440
cgagaccact gagcccacca ttccggtaga gcccactgat cctgcagaac ctac         1494
```

<210> SEQ ID NO 26
<211> LENGTH: 2619
<212> TYPE: DNA
<213> ORGANISM: Artificial Sequence
<220> FEATURE:
<223> OTHER INFORMATION: Unknocked out ExeR gene PCR (DNA)

<400> SEQUENCE: 26

| | | |
|---|---|---|
| gtgagaccaa aggtgaactg ccaggtcgac caaattgctc gccaagcaga ctccgaaaaa | 60 |
| cacgggtaat tcatatggct tgtatctaat ccatactgaa cagaggacct ctcctatgtc | 120 |
| tcgcatttct gcgcgcactc tggcaatcgc acttgccggt gcaaccgcgg ccagcctggc | 180 |
| agttgttcca gcagcaacag ctaatcctgc cggaaccgct cctgtcatca acgaaatcta | 240 |
| cggaggcggt ggaaacagcg gatcgttgtt ctccaacgac ttcattgagc tctacaaccc | 300 |
| aacctcaggg gacatttccc tcgacggttg gagcgttacc tactacgcag ccaacggtaa | 360 |
| ctccggcgga accacaaacc tgaccggaaa catccctgcc aacggttact acctcatcca | 420 |
| gcaacgcgca ggcagcaaca caccggcgc tctgcctacc ccagacgcca ccggtaactt | 480 |
| ggcaatgggt gcctcccaag gatcagttgc actgaccgac aactctggcc taaccgctga | 540 |
| ccttgtcgga ttcggtggca cgtccatgtt tgaaggaaca gctgctgcac ctgagaccag | 600 |
| caacaaattg tctgttcaac gcaaagaagt tggcgctgac tctgataaca actccgtaga | 660 |
| cttcgagact ggagctccaa ctccaacgtc tcgggagga tccgctcctg ttgacccagg | 720 |
| cgagccagaa actccagtaa accctgggga acagtctcc atcgcacaaa tccaaggaac | 780 |
| cggtctcgct accccactcg agggtcagac cgtcaccacc gaaggtattg tcactgccgt | 840 |
| ttacgcagaa ggtggcttca cggttacta catccagaca cctggatctg gtactgcacc | 900 |
| aaaggttgct ggcgacgcat ccgacggcat cttcgtctac gtgggaagca atggttccta | 960 |
| cccagagctc ggcgcatctg tcaccgtcac tggcaaggcc accgaacact acgagatgac | 1020 |
| tcagctaggc aactcctcct tcaccgtttc ggacaccgca ttcgagccag taacccccact | 1080 |
| cgaactggac accgttccta ctggcgatga cattcgcgaa gcatacgaag gcatgctgct | 1140 |
| gaagccaacc ggcgctcaca ccgtgaccaa caactacgca accaacaccct tcggtgaaat | 1200 |
| tgccctcgcc ccaggtaacg agcctttgta ccaggccact caaatggtgg caccgggagc | 1260 |
| cgaagcgatt gcgtacgagg cggaaaacgt cgcaaagcaa attacgctgg atgacggacg | 1320 |
| ctccggcaac tacactcgcg gcgactccag cacgcctatg gcatggcttg tgcaggacgg | 1380 |
| tggcgagacc atcaagtcca tccgcaccgg cgaccaggtg gaattccagg caccagtaat | 1440 |
| cttcgattac cgctacgacc tgtggaaatt ccagccaacc acccctgtca ccggcaacac | 1500 |
| cgcaagctcc gaccttccta tcacctggga tgacacccgc gcggctgagc tagcttcaat | 1560 |
| caatgacgtt gctggcgaat tccacatcgc aagcttcaac gtgctcaact acttcacctc | 1620 |
| tctcggcgaa gatgaaccag gctgcagcgc atacagggat atcaacaaca ccccagtcac | 1680 |
| cgccaacaac tgtaacgtcc gtggcgctta caccgaagaa gcactcgaag atcagcagag | 1740 |
| caagatcgtc gaagcaatca accgccttga cgtcgatgtt cttggacttg aagaaatcga | 1800 |
| aaacaccgcg accgtcaccg cgacgtctc cgtcgcgat gacgcactca taccctcgt | 1860 |
| cgcagcactc aacgaagcag ttggatccga tcgctgggcg gccgtcgaat ctccagaaca | 1920 |
| attgggcacc gatgaagact acatccgcgt cgccttcatc tacgaccaaa ccaccgtcaa | 1980 |
| gcccgtcggc gaatcccgaa tcttcgacga cgcagccttc accggcaccg cacgccagcc | 2040 |
| actcgcacag gaattccagc cactcaacga cagcgagaaa tccttcgtcg gcgtagtcaa | 2100 |

```
ccacttcaag tccaagggct ctgtcactcg tggagacgcc gacaccggcg acggccaagg    2160
caacaacgcc aacgttcgcg tcgcacaggc acaggcactc atcgaccacc tggaaaacca    2220
ggacgactgg gcatccaagc caatcttcat cctcggcgac accaactcct acgccaagga    2280
aaccgcgatg accacccttt acggcgctgg ctacaccaac atcgccaccg aattcgacgc    2340
tggctacagc taccagttct ccggccgcat tggcagcctc gaccacgcac tcggcaacga    2400
agcagccatg aagcacgtca tcgacgccga ggtctgggac atcaacgctg acgaagcaat    2460
cgcattcgaa tactcccgtc gactcaacaa cacctccgac gtattcgaga caacgtcttt    2520
ccgctcctcc gaccacgacc cgatcaaggt cggattcaac ctcagcgaga ccactgagcc    2580
caccattccg gtagagccca ctgatcctgc agaacctac                          2619
```

<210> SEQ ID NO 27
<211> LENGTH: 11982
<212> TYPE: DNA
<213> ORGANISM: Artificial Sequence
<220> FEATURE:
<223> OTHER INFORMATION: Plasmid (pJYS3_crtYf)

<400> SEQUENCE: 27

```
taattatcat tgactagccc atctcaattg gtatagtgat taaaatcacc tagaccaatt      60
gagatgtatg tctgaattag ttgttttcaa agcaaatgaa ctagcgatta gtcgctatga     120
cttaacggag catgaaacca agctaatttt atgctgtgtg gcactactca accccacgat     180
tgaaaaccct acaaggaaag aacggacggt atcgttcact tataaccaat acgctcagat     240
gatgaacatc agtagggaaa atgcttatgg tgtattagct aaagcaacca gagagctgat     300
gacgagaact gtggaaatca ggaatccttt ggttaaaggc tttgagattt tccagtggac     360
aaactatgcc aagttctcaa gcgaaaaatt agaattagtt tttagtgaag agatattgcc     420
ttatcttttc cagttaaaaa aattcataaa atataatctg gaacatgtta agtcttttga     480
aaacaaatac tctatgagga tttatgagtg gttattaaaa gaactaacac aaaagaaaac     540
tcacaaggca aatatagaga ttagccttga tgaatttaag ttcatgttaa tgcttgaaaa     600
taactaccat gagtttaaaa ggcttaacca atgggttttg aaaccaataa gtaaagattt     660
aaacacttac agcaatatga aattggtggt tgataagcga ggccgcccga ctgatacgtt     720
gattttccaa gttgaactag atagacaaat ggatctcgta accgaacttg agaacaacca     780
gataaaaatg aatggtgaca aaataccaac aaccattaca tcagattcct acctacataa     840
cggactaaga aaaacactac acgatgcttt aactgcaaaa attcagctca ccagttttga     900
ggcaaaattt ttgagtgaca tgcaaagtaa gcatgatctc aatggttcgt tctcatggct     960
cacgcaaaaa caacgaacca cactagagaa catactggct aaatacggaa ggatctgagg    1020
ttcttatggc tcttgtatct atcagtgaag catcaagact aacaaacaaa gtagaacaa     1080 ctgttcaccg ggcccgtggg tggctaggca agttacagaa ctgatcggat aaaagcagag    1140
ttatatctga tgaattgcta ttagcagtat cgttatcaca gcaccaacaa agtagttcag    1200
ccacaggaaa actttccaac tgcgattagc ctgttcacaa ctggcatctg taatgttcca    1260
aaatcgtgcg gcattaaata cgtaagttag aatcgcaatc ccgatgatcc acgccggatt    1320
aggcaaagta gtgactaaca cagcagctag taaataaagt actactgaaa gccgaatggc    1380
tccacgcgcc ccaattacag tggcaattga gctcagatta gcttcccggt ctgcattaac    1440
atcctgtact gctccaagga tctgactggc catgccccac aagaaaaagg atcccagtgc    1500
tatccacatc gctgctgaag gagatgttcc agtgatcgtt gcaccgatta atgcaggtga    1560
```

```
agtgaagtga gtagaagatg ttagagcatc gataaagggg cgttctttaa aacgcaatttt    1620 cggtgctgaa taagcaatca ctgctagcac tgagagtgtc agccataaag acgacatcca    1680
ggtgccaaat atgaaaagaa taactaggaa aggaattgtt gagatagccg aggcccataa    1740
cagtgtgctg tgggaacttt tcggtagcac ggccccctcg acgccgcctt tgcggggatt    1800
acgcatatca gattcgtaat caaaaacatc gttgatacca tacatggcga tgttatacgg    1860
gataagaaaa aatacgatgc ctagccaaaa cagccagtca atctctcctg catttaatag    1920
gtaggccaga ccaaaggggt aggcggtatt gatccagcta atggggcgag atgacaatag    1980
aattagtctt attttttcca tcatgactac ggcttttctg gctcagattg cgtggtggtg    2040
gatcgcaccc aatgagaact aggagagtac ctagataaat aaaggccata aaaatatcgc    2100
tatcttgctc attttgtgaa atatcgatga tagggatcaa aatttaatga tcgtatgagg    2160
tcttttgaga tggtgtcgtt ttaggcggca atggttcggg cagtggtcct gcactggtat    2220
cggcatgtaa acgcttaata atattctcgg cagaaattaa acacatgggt attcctacac    2280
ccgggacggt ggtggcaccg aatagaagga ggttattgac cttgcgggag ctattgcgcc    2340
ctcttaagaa agcggactgt ctgagggtat gtgctggacc cagcgcactg cctacccatg    2400
aatggtagcg gtgctcaaaa tccgcagggc caatggtgcg tttgaccaca attcggtcag    2460
tgaggtcagg gatgccggct tgcgtagcaa tttgattgat tgcatgtgac gcgattgttt    2520
ccacggatgc tgaagccgac tgcatatacg catcaccgtg gccgatgctg ctagaggcct    2580
tggtcggaat taaaacaaaa aggttttcgt atccagcagg tgcaacgccg tcttcggacg    2640
ttgaaggctt ggagacataa atggaatttg atgcattgtg ggggcgggta agttgaggcc    2700
cgtcgaaaac tacagcaaaa tcatctgtcc aatcttcact gaagaaaagg ttgtgatggt    2760
cgagctgggg taactctcct tttacgccca ggaggattaa taccgctcca attccaggat    2820
tgcgattgga ccaatatcgt tcgggatagg ttcgaagttc ccggggaagc agattatttt    2880
ctgtatggtg taggtcgcct gctgaaacca caagatccgc atctagattt tgcacttttc    2940
tgttgtgaag caagctcaca cctgtggcgc ttgtgttgcc cctcgatgaa gcagtgttga    3000
tggaaatgac ctcagaatcg agttgaaact caaccccgtt ttccagcgct aactgatgca    3060
gagcgttaac cactgcagta aaaccaccta tagggtattt cactccctgc accaaatcgg    3120
tatgactcat caagtggtac atcgatgggg tagtagtggg tcgggaagac aggaagactg    3180
ctggataggc tagattgaca gctagctcag tcctaggtat aatggatccg aatttctact    3240
gttgtagatc aggcaaccat agggcaggaa atttaaataa aacgaaaggc tcagtcgaaa    3300
gactgggcct ttcgttttat ctgttgtttg tcggtgaacg ctctcctgag taggacaaat    3360
ccgccgggag cggatttgaa cgttgcgaag caacggcccg gagggtggcg ggcaggacgc    3420
ccgccataaa ctgccaggca tcaaattaag cagaaggcca tcctgacgga tggcctttt    3480 gcgtttctac aaactcttaa gcttgcatgc ctgcaggtcg acttagttat tgcggttctg    3540
gacaaattca aagtattctt cgttcttaat gacgagattc agcttcttgc cttcctggtt    3600
gttcttgatg cgacccagga gcatgagacc cttcagaccg atgtggtagg cgccgttttgc    3660 atcagcgtcc tgtggcatgt tctttggagc ctggcgggaa tcgaagaagt tgccgttgac    3720
gtcggccact ggggagatga ggtaatccag ctcggtgccg gtcttggagt tgcgcatctg    3780
caggatggtg ttgagcacag aggtcagctt tgcgaagaac ttcttgtcgg attcgccgca    3840
gattgcagcc ttgatgcact cgccgtggcc gtattcgatg gagtaatcct tcaggagctt    3900
ctccagttcc ttggttgggt acacttcgcg ggtatcccag ttgtggttct tgtcggagtt    3960
```

```
gcggaagttg atgaggcggg agccgaagga tgcgatggtc cacttgccct tggctgcctt    4020
atcgccgaag ttcttgtagt cgaaggagaa ttcgaagtag cccttatcca ggttgtagca    4080
gatcttgtcg aacttggaga agaactcctg ggacttggag acggattcgt actttgggta    4140
gagctggttg acgaagccgg tcactgggca gatcttagag gtgaagccag ctggcacgta    4200
gtagatgatg ccggtctgct tgcccatctt cttgaaggtc tcgaatgggg cggtcagctg    4260
gtatgcacgg aggacgccgc cggtcttatc gaattcgttg tccttgaaca cgaggtagtt    4320
cagcttctcg atgagcatct tttccagctt ctggtagacc tgcttctcca ccttgaagcg    4380
gccgcgcttg aagccgaagt tcaggtcttc gaagaccacg attgcgttgt actcgatcac    4440
cagcttagcg atttcgtgga ccacctggga gaggtagcct tccttcattt ccttgatgtt    4500
gttgatcttc ttccaatcct tgcgagcgga atcgcggtcc ttctcgatag cggccagctt    4560
gtcgtggtag ttggtcttca tgcgatcgtt gccgatgatg ttgaaggtgt cctgcttgat    4620
gatgttgccc ttgccgtcga ccagggtgta gtaggcgagg tggcgttcgc cgcgatcgat    4680
ggacaggatg tgcacgtcgt tagccttctc cttcaggagc aggttgattt catcgttgaa    4740
cttgttggcg ccggaggact tgaagttgat ggtgattggg cagtggaaga agaacttgtc    4800
ctcggtgaag cgcttatcct tgatcaggtc gtactcgaac acggattcct tctttgggtt    4860
atccttgttc ttgttggcga ttgcttcctt ggctgggtgg gtgatcttct ttgggatgga    4920
ctgcttgcgg tagaacagct ctgcttcgcc gttgagcttg tagaccacat cctgcaggtt    4980
gcgttcgtcg aagagtgcct tccagtagag ggtgtgcagg tttgggcggc ccttggagta    5040
agcggagaag tccttgttgt agatctggaa gaggtacagc ttgccctggt tgaccacgga    5100
atcgatgtag gactcggaga tgttttcgaa ggtcagcttg tagccctggt tctccacttc    5160
gcggtagaat tcatcgatgg agttgtagcg ctgggtatcg agaagcggaa agccgaagtc    5220
cttccactct gggtgcttgg agatggactg cttgtagaaa tcgatgaact tgcggcagtc    5280
ttcgatgttg aactcgaact tttcgtagcc cttctgtggg gagccgttct tggtgtgggt    5340
ggagtggttg cggatgcgca ggatatcttc ggatgggttg tagaacttga tggactttgc    5400
ggagaagaag acctttggga gcatcttgtt agcgcctggg agcagcttgt acacgatctt    5460
cttgtagccc tcgcccttgt tttccttgat ggccttatcg tcgaagatct tgttgttctt    5520
cttgttcatc acgcccaggt agtacttatc gtccttgatg aagaggatgg cggtgttatc    5580
tggttccttg ttcttgtccc agccgtttgc cagggtggag ttctcgaagt tgagcttgaa    5640
cttttcatcg gagtatggct tctgggtgat gtagttgcgg atcttgttgt acagtgggac    5700
gatgttagcg agttcgaagt agcactcttc gaacaccagg tagaagtgct catccttgtc    5760
gaggatgttg gccttgtctt cggactggga gatgtgaaag atcttcagct tgtggagcag    5820
gttgttggtc tgatcgagca ggtccttgat tgccttcaca tcgtcctcag cggaggcctg    5880
gagcagatcc ttcttgccct ggttctgtta cttgatggag atctgggcca ggttatcctt    5940
gttctgtgcg atttcgtcga agatcattgg gattgcagcg aagtttgcga ggatctcttc    6000
gaagcggcac tgcttatcga tgtcgcggtg cttgttgaac tcttcgagag ccagcttgat    6060
ggtctcgagg gacaggtact tagccttttc ggtcttcttg gcgatcagct cctgttcctt    6120
cttggatggg ttatcgaggt ctttggggc gatctgctgg gtgatgtatt ccaggactgc    6180
ggtgccgatc acggagtaat cgtcgaagac ctgctgggag agatcggtca gggacttgtc    6240
gttcttgaag tagatcttgg agagatccag cttctgagcc ttcagatcgt cgaagagcag    6300
ggagagggtc tccttgatgg acttctcttc cacggtcttg aaggctgcga tctgttcgta    6360
```

```
gaaggactgc atggtggtga ccacatcgga atcgtcctcc agcttgtcga tgacgaagga   6420
cttggattcg gtgtcggaca ggatctgctt gaagagcacg gacatcttgt acttcttcag   6480
ggtcttatcg ttgatctgct gggagtagag gttgatgtac tcgttgatgc ccttgcgctt   6540
ggtgttttcg ccgttgacga acttgccgcc gatgatggtg ttgaacttgg tgatgccgga   6600
ctggttcagg tagttgttga agttggcgat ctcgaacact tcatcgaggg agaagacgcg   6660
ctggttcact tcagaggtct tgtaatcgat gtcgaaggtg agctcttcgg ccaggtcctt   6720
cttgatctgc tcgtagttga tagcttctgg ggccttatcc ttcagggact cgtactttgc   6780
cttgttttcg aggaactttg gcaggttatc gtcgacgatg cggtagatga tagaggttgg   6840
gatatcgttg gaggagtaca cgttcttgcg gttttcgtgg aagcccttga agtaggtggt   6900
ccagcccttg aaggacttga tgatctccag agcttcatcg atgtcggtga tgtcggagtt   6960
ggccttgaag agctcgatgc cgttatcctt ggactgcttg agccacagga tgagatcgga   7020
ttcctggccc ttctttgcgt cgatcaggtt ctggttgaag aggttcttga acttctcgga   7080
atccttgatg tattcggaga tctgcttctt gatggtatcc ttagcggact tgaagtcctt   7140
ctgcaggtta tcgtcatcgg acttcttgag cttgaagtag acatcggagt agttctggag   7200
caggtcctcg gagatgcaca cggaggacag gatctcttcg atgaagaact ggtggtactt   7260
gtcgatgatc tgctttgcct tcttgtaatc cttagcgcgc ttttcgtcat ccaggatgag   7320
gccgcgtgcc ttgatgtttt cgagggtctt gccttggggg atcagctcaa acgagggt    7380 cttggacagg gagtatttat tcacaaactc ttggtagatg acatcgttc aagtcctttc    7440 caattccaca catggtacca cacgatgatt aattgtaaac agctcaggtc atgattccgc   7500 gaacccaga gtcccgctca gaagaactcg tcaagaaggc gatagaaggc gatgcgctgc    7560 gaatcggag cggcgatacc gtaaagcacg aggaagcggt cagcccattc gccgccaagc    7620
tcttcagcaa tatcacgggt agccaacgct atgtcctgat agcggtccgc cacacccagc   7680
cggccacagt cgatgaatcc agaaaagcgg ccatttttcca ccatgatatt cggcaagcag   7740
gcatcgccat gggtcacgac gagatcctcg ccgtcgggca tccgcgcctt gagcctggcg   7800
aacagttcgg ctggcgcgag cccctgatgc tcttcgtcca gatcatcctg atcgacaaga   7860
ccggcttcca tccgagtacg tgctcgctcg atgcgatgtt tcgcttggtg gtcgaatggg   7920
caggtagccg gatcaagcgt atgcagccgc cgcattgcat cagccatgat ggatactttc   7980
tcggcaggag caaggtgaga tgacaggaga tcctgccccg gcacttcgcc caatagcagc   8040
cagtcccttc ccgcttcagt gacaacgtcg agcacagctg cgcaaggaac gcccgtcgtg   8100
gccagccacg atagccgcgc tgcctcgtct tggagttcat tcagggcacc ggacaggtcg   8160
gtcttgacaa aaagaaccgg gcgccctgc gctgacagcc ggaacacggc ggcatcagag    8220
cagccgattg tctgttgtgc ccagtcatag ccgaatagcc tctccaccca gcggccgga    8280 gaacctgcgt gcaatccatc ttgttcaatc atgcgaaacg atcctcatcc tgtctcttga   8340
tcagatcttg atcccctgcg ccatcagatc cttggcggca agaaagccat ccagtttact   8400
ttgcagggct tcccaacctt accagagggc gccccagctg gcaattccgg ttcgcttgct   8460
gtccataaaa ccgcccagtc tagctatcgc catgtaagcc cactgcaagc tacctgcttt   8520
ctctttgcgc ttgcgttttc ccttgtccag atagcccagt agctgacatt catccgggt    8580 cagcaccgtt tctgcggact ggctttctac gtgttccgct tcggtgacc gcctcgatga    8640 tcgccgggtg ggcgtggccc aaggaggatc atccagccat tcggggtcgt tcactggttc   8700 cccttttctga tttctggcat agaagaaccc ccgtgaactg tgtggttccg ggggttgctg   8760
```

```
atttttgcga gacttctcgc gcaattccct agcttaggtg aaaacaccat gaaacactag      8820
ggaaacaccc atgaaacacc cattagggca gtagggcggc ttcttcgtct agggcttgca      8880
tttgggcggt gatctggtct ttagcgtgtg aaagtgtgtc gtaggtggcg tgctcaatgc      8940
actcgaacgt cacgtcattt accgggtcac ggtgggcaaa gagaactagt gggttagaca      9000
ttgttttcct cgttgtcggt ggtggtgagc ttttctagcc gctcggtaaa cgcggcgatc      9060
atgaactctt ggaggttttc accgttctgc atgcctgcgc gcttcatgtc ctcacgtagt      9120
gccaaaggaa cgcgtgcggt gaccacgacg ggcttagcct ttgcctgcgc ttctagtgct      9180
tcgatggtgg cttgtgcctg cgcttgctgc gcctgtagtg cctgttgagc ttcttgtagt      9240
tgctgttcta gctgtgcctt ggttgccatg ctttaagact ctagtagctt tcctgcgata      9300
tgtcatgcgc atgcgtagca aacattgtcc tgcaactcat tcattatgtg cagtgctcct      9360
gttactagtc gtacatactc atatttacct agtctgcatg cagtgcatgc acatgcagtc      9420
atgtcgtgct aatgtgtaaa acatgtacat gcagattgct gggggtgcag ggggcggagc      9480
caccctgtcc atgcggggtg tggggcttgc cccgccggta cagacagtga gcaccggggc      9540
acctagtcgc ggatacccc cctaggtatc ggacacgtaa ccctcccatg tcgatgcaaa       9600
tctttaacat tgagtacggg taagctgcca cgcatagcca agctaggcgg ccaccaaaca      9660
ccactaaaaa ttaatagtcc ctagacaaga caaaccccg tgcgagctac caactcatat       9720
gcacggggc cacataaccc gaaggggttt caattgacaa ccatagcact agctaagaca       9780
acgggcacaa cacccgcaca aactcgcact gcgcaacccc gcacaacatc gggtctaggt      9840
aacactgaaa tagaagtgaa cacctctaag gaaccgcagg tcaatgaggg ttctaaggtc      9900
actcgcgcta gggcgtggcg taggcaaaac gtcatgtaca agatcaccaa tagtaaggct      9960
ctggcggggt gccataggtg gcgcagggac gaagctgttg cggtgtcctg gtcgtctaac     10020
ggtgcttcgc agtttgaggg tctgcaaaac tctcactctc gctgggggtc atctctggct     10080
gaattggaag tcatgggcga acgccgcatt gagctggcta ttgctactaa gaatcacttg     10140
gcggcgggtg gcgcgctcat gatgtttgtg ggcactgttc gacacaaccg ctcacagtca     10200
tttgcgcagg ttgaagcggg tattaagact gcgtactctt cgatggtgaa acatctcag      10260
tggaagaaag aacgtgcacg gtacggggtg gagcacacct atagtgacta tgaggtcaca     10320
gactcttggg cgaacggttg gcacttgcac cgcaacatgc tgttgttctt ggatcgtcca     10380
ctgtctgacg atgaactcaa ggcgtttgag gattccatgt tttcccgctg gtctgctggt     10440
gtggttaagg ccggtatgga cgcgccactg cgtgagcacg gggtcaaact tgatcaggtg     10500
tctacctggg gtggagacgc tgcgaaaatg gcaacctacc tcgctaaggg catgtctcag     10560
gaactgactg gctccgctac taaaaccgcg tctaaggggt cgtacacgcc gtttcagatg     10620
ttggatatgt tggccgatca aagcgacgcc ggcgaggata tggacgctgt tttggtggct     10680
cggtggcgtg agtatgaggt tggttctaaa aacctgcgtt cgtcctggtc acgtgggct      10740
aagcgtgctt tgggcattga ttacatagac gctgatgtac gtcgtgaaat ggaagaagaa     10800
ctgtacaagc tcgccggtct ggaagcaccg gaacgggtcg aatcaacccg cgttgctgtt     10860
gctttggtga agcccgatga ttggaaactg attcagtctg atttcgcggt taggcagtac     10920
gttctcgatt gcgtggataa ggctaaggac gtggccgctg cgcaacgtgt cgctaatgag     10980
gtgctggcaa gtctgggtgt ggattccacc ccgtgcatga tcgttatgga tgatgtggac     11040
ttggacgcgg ttctgcctac tcatgggac gctactaagc gtgatctgaa tgcggcgtg      11100
ttcgcgggta atgagcagac tattcttcgc acccactaaa agcggcataa accccgttcg    11160
```

```
atattttgtg cgatgaattt atggtcaatg tcgcggggggc aaactatgat gggtcttgtt    11220
gttggcgtcc cggagcgtaa aggatctagg tgaagatcct ttttgataat ctcatgacca    11280
aaatccctta acgtgagttt tcgttccact gagcgtcaga ccttgatgat accgctgcct    11340
tactgggtgc attagccagt ctgaatgacc tgtcacggga taatccgaag tggtcagact    11400
ggaaaatcag agggcaggaa ctgctgaaca gcaaaaagtc agatagcacc acatagcaga    11460
cccgccataa aacgccctga gaagcccgtg acgggctttt cttgtattat gggtagtttc    11520
cttgcatgaa tccataaaag gcgcctgtag tgccatttac ccccattcac tgccagagcc    11580
gtgagcgcag cgaactgaat gtcacgaaaa agacagcgac tcaggtgcct gatggtcgga    11640
gacaaaagga atattcagcg atttgcccga gcttgcgagg gtgctactta agcctttagg    11700
gttttaaggt ctgttttgta gaggagcaaa cagcgtttgc gacatccttt tgtaatactg    11760
cggaactgac taaagtagtg agttatacac agggctggga tctattcttt ttatctttt    11820 ttattctttc tttattctat aaattataac cacttgaata taaacaaaaa aaacacacaa    11880
aggtctagcg gaatttacag agggtctagc agaatttaca agttttccag caaaggtcta    11940
gcagaattta cagataccca caactcaaag gaaaaggact ag                       11982
```